United States Patent
Dallemagne et al.

(10) Patent No.: US 9,663,465 B2
(45) Date of Patent: May 30, 2017

(54) ACETYLCHOLINESTERASE INHIBITORS AND PROMNESIANT SEROTONIN 5-HT4 RECEPTOR AGONISTS, THEIR METHODS OF PREPARATION AND THE PHARMACEUTICAL COMPOSITIONS CONTAINING THE SAME

(71) Applicant: UNIVERSITE DE CAEN, Caen (FR)

(72) Inventors: Patrick Dallemagne, Saint Georges d'Aunay (FR); Christophe Rochais, Caen (FR); Cedric Lecoutey, Caen (FR); Michel Boulouard, Douvre la Delivrande (FR); Thomas Freret, Amaye sur Orne (FR)

(73) Assignee: UNIVERSITE DE CAEN (FR)

( * ) Notice: Subject to any disclaimer, the term of this patent is extended or adjusted under 35 U.S.C. 154(b) by 0 days.

(21) Appl. No.: 14/895,731

(22) PCT Filed: May 19, 2014

(86) PCT No.: PCT/FR2014/051149
§ 371 (c)(1),
(2) Date: Dec. 3, 2015

(87) PCT Pub. No.: WO2014/195593
PCT Pub. Date: Dec. 11, 2014

(65) Prior Publication Data
US 2016/0122300 A1    May 5, 2016

(30) Foreign Application Priority Data
Jun. 5, 2013 (FR) ..................... 13 55155

(51) Int. Cl.
C07D 211/34 (2006.01)
C07D 211/20 (2006.01)
C07D 211/26 (2006.01)
C07D 211/32 (2006.01)

(52) U.S. Cl.
CPC .......... *C07D 211/34* (2013.01); *C07D 211/20* (2013.01); *C07D 211/26* (2013.01); *C07D 211/32* (2013.01)

(58) Field of Classification Search
None
See application file for complete search history.

(56) References Cited

FOREIGN PATENT DOCUMENTS

WO    WO 9427965 A1 * 12/1994 .......... C07C 225/22

OTHER PUBLICATIONS

Cho, S et al Exp Neurol 2006 vol. 203 pp. 274-278.*
Eglen, R et al Br J Pharm 1995 vol. 115, pp. 1387-1392.*

* cited by examiner

*Primary Examiner* — Heidi Reese
(74) *Attorney, Agent, or Firm* — Gerald E. Hespos; Michael J. Porco; Matthew T. Hespos

(57) ABSTRACT

Compounds are provided according to Formula (I)

(I)

as well as their enantiomers and their racemics, their acid salts, their hydrates or their solvation products. Among a large number of possible meanings, X represents a halogen, Y an oxygen atom; all of the coefficients m, n, r and s have the value 1, R represents an ethyl and R' a cycloalkyl. The invention also includes Methods of preparing the above compounds and the pharmaceutical compositions containing them also are provided.

14 Claims, 1 Drawing Sheet

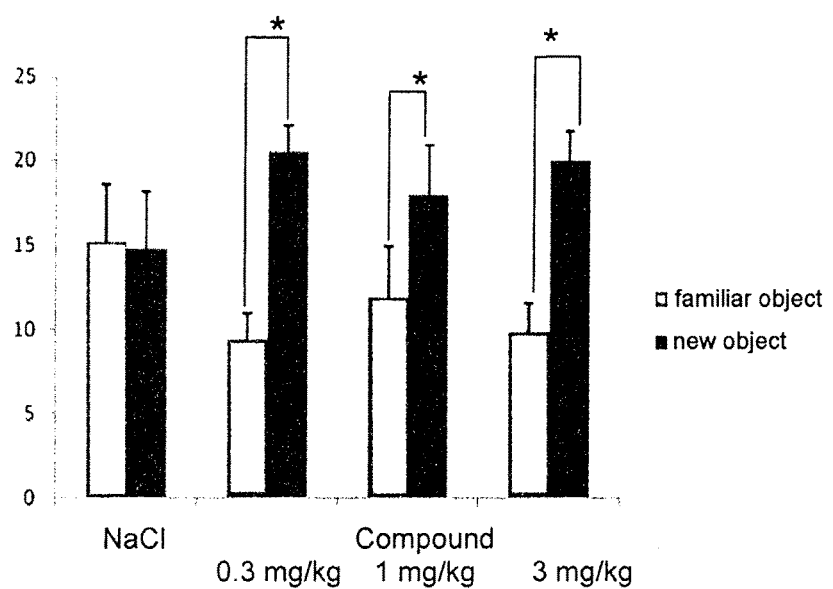
Compound 9 improves the mouse's memory performance in the object recognition test. N=12 per group. *p<0.05 versus familiar object (ANOVA then Newman-Keuls test).

ACETYLCHOLINESTERASE INHIBITORS AND PROMNESIANT SEROTONIN 5-HT4 RECEPTOR AGONISTS, THEIR METHODS OF PREPARATION AND THE PHARMACEUTICAL COMPOSITIONS CONTAINING THE SAME

BACKGROUND

1. Field of the Invention

This invention concerns novel derivatives of 3-(piperidin-4-yl)-1-(4'-amino-phenyl)propan-1-one as well as their use as a promnesiant drug in the treatment of neurological diseases with memory deficits. This invention has unexpectedly revealed that mixed acetylcholinesterase catalytic and peripheral inhibitors and serotonin 5-HT4 receptor agonists have promnesiant and, in particular, "anti-Alzheimer" activities.

2. Related Art

Numerous diseases and accidents can cause an amnestic syndrome:
- progressive amnesia associated with dementia such as Alzheimer's Disease (AD) and vascular dementia;
- cranial traumas (permanent or temporary post-traumatic amnesia);
- cerebrovascular accidents;
- Korsakoff syndrome;
- brain tumors or injuries;
- other causes linked to recurrent long-term illnesses such as epilepsy.

AD has become the 4th cause of death in industrialized countries and there are currently no drugs on the market that appear to be capable of having a curative effect. Most of them are in fact acetylcholinesterase inhibitors (AChE) whose effectiveness is fairly poor and tolerance mediocre. It now seems necessary to associate with this symptomatic effect a curative effect by using compounds that have a plurality of actions (Multi Target Directed Ligands or MTDL).

Different MTDLs targeting AD are currently being studied. However, none of these works has yet combined in one structure an anti-AChE activity and a 5-HT4 agonist activity, even though AChE inhibitors and 5-HT4 agonists, independently of or in association with each other[ii] have shown promnesiant properties. Now this dual effect appears to be extremely promising in MTDL chemotherapy of AD. In fact, this approach can allow a symptomatic effect to be produced by using just one active ingredient, linked to the restoration of cholinergic transmission by the catalytic inhibitory action of AChE[i], as well as a potentially curative dual effect. This is due, on the one hand, partly to the promotion of the non-amyloidogenic cleavage of the β-A protein precursor and, consequently, the formation of the neurotrophic sAPP-α, in connection with a 5-HT4 agonist effect[i]. On the other hand, this curative effect could also be attributable to the inhibition of a second role recently identified for AChE, that of promoting amyloid aggregation by interaction between the β-A protein and a peripheral site of the enzyme.

SUMMARY

This invention concerns the development of novel drugs capable of having, particularly through both catalytic and peripheral inhibition of acetylcholinesterase and an agonist to serotonin 5-Ht4 receptors, a real promnesiant effect and therefore constitutes a novel opportunity to treat, amongst other things, Alzheimer's disease. It has been discovered that the compounds of formula (1), as defined below, achieve this aim.

To the knowledge of the inventors, the compounds of formula (1), defined below, have so far never been described and form part of the invention as novel products. The said compounds of formula (1) have a novel mechanism of action combining both the catalytic and peripheral inhibition of AChE and the stimulation of 5-HT4 receptors. The novelty of this mechanism of action to combat, amongst other things, Alzheimer's disease also forms part of the invention.

DETAILED DESCRIPTION

Thus, according to a first of its aspects, this invention relates to a compound of the general formula (I):

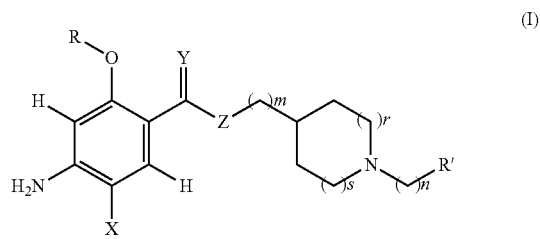

wherein:

X represents
- a hydrogen atom, or
- a halogen atom (Hal), where (Hal) is fluorine, chlorine, bromine or iodine, or
- a straight- or branched-chain $C_pHal_{2p+1}$ polyhalogenoalkyl group, where p=1, 2, 3 or 4 (Hal), having the same meaning as indicated above;

Y represents
- an oxygen atom, or
- a sulfur atom, or
- an N—R" radical where R" represents a hydrogen atom, an —OH radical, a straight- or branched-chain $C_qH_{2q+1}$ alkyl radical, where q=1, 2, 3 or 4, or
- a —OR''' radical where R''' represents a straight- or branched-chain $C_qH_{2q+1}$ radical, where q=1, 2, 3 or 4;

Z represents
- a straight- or branched-chain C1-C6 alkyl radical, or
- an N—R" radical where R" represents a hydrogen atom or a straight- or branched-chain $C_qH_{2q+1}$ alkyl radical, where q=1, 2, 3 or 4, or
- an oxygen atom, or
- a sulfur atom;

( )m represents a number m of methylene group(s), whose value is 1, 2 or 3

( )n represents a number n of methylene group(s), whose value is 0, 1, 2 or 3

( )r and ( )s represent a number r and s respectively of methylene group(s), whose values are: r=s=0; or r=s=1; or r=s=2; or r=0 and s=1; or lastly r=0 and s=2;

R represents
- a hydrogen atom or
- a straight- or branched-chain C1-C5 alkyl group, capable of carrying one or more F atoms R' represents
- a straight- or branched-chain C1-C6 alkyl radical, or
- a C3-C10 cycloalkyl or C5-C13 bicyclic group, capable of carrying one or more R groups and of possessing an oxygen atom, or a nitrogen atom that can be substituted by R, or a sulfur atom or a radical such as —SO$_2$— or —SO— or a CH$_2$NHSO$_2$R'''' radical, where R'''' represents a straight- or branched-chain C1-C5 alkyl group, capable of carrying one or more F atoms, as well as its enantiomers and its racemics, its acid salts, its hydrates or its solvation products.

As can be seen from the following examples, the compounds of formula (I) according to the invention have particularly interesting properties as regards memory impairment symptoms, including those of Alzheimer's disease.

According to one embodiment, in formula (I), X represents a halogen atom.

According to another embodiment, in formula (I), Y represents an oxygen atom.

According to another embodiment, in its formula (I), Z represents a methylene group or a CH—CH$_3$ group.

According to another embodiment, in its formula (I), all of the m, n, r and s coefficients have the value 1.

According to another embodiment, in formula (I), R represents H, CH$_3$, CH$_2$CH$_3$ or CH$_2$—CH$_2$F According to another embodiment, in formula (I), R' represents a radical taken from the group formed by the n-propyl, cyclopropyl, cyclobutyl, cyclopentyl, cyclohexyl, 4-piperidine, —CH$_2$NHSO$_2$CH$_3$ radicals.

According to another embodiment, in formula (I), R represents a methyl radical and R' a C$_4$-C$_7$cycloalkyl radical.

The invention also includes several methods of preparing the compounds of formula (I).

The invention also therefore relates to a first method of preparing the compounds of formula (I) for which R=CH$_3$, Y=0 and Z, X, m, n, r, s and R' have the meanings previously described for formula (I), characterized in that a) carbonyldiimidazole, then potassium ethyl malonate are reacted in tetrahydrofuran in the presence of magnesium chloride with a 4-amino-2-methoxybenzoic acid to obtain a compound of the general formula (II)

(II)

a formula wherein X has the same meaning as that indicated for formula (I);

b) the compound (II) thus obtained is reacted with a tertiary butyl 4-(halogenoalkyl)piperidine-1-carboxylate in dimethylformamide in the presence of potassium carbonate, then with potassium hydroxide in an ethanol/water mixture to obtain a compound of general formula (III)

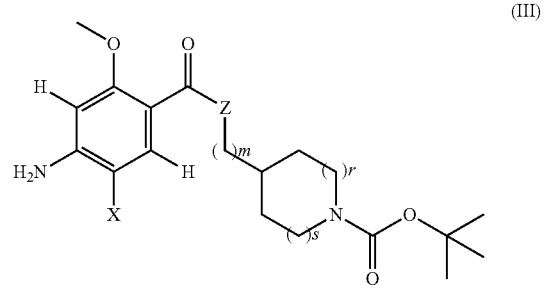

(III)

a formula wherein Z represents a methylene group and X, m, r and s have the same meanings as those indicated for formula (I);

c) the compound of formula (III) obtained in the preceding stage is reacted with trifluoroacetic acid in dichloromethane then with an alkyl or N-substituted 4-alkylpiperidine halide in the presence of an excess of potassium carbonate in dimethylformamide, which enables the desired compounds of formula (I) to be obtained.

The invention also covers a second method characterized in that a) a 4-amino-3-methoxybenzoic acid is reacted with a tert-butyl 4-(aminoalkyl)piperidine-1-carboxylate in the presence of hydroxybenzotriazole, ethyl-3-(3-dimethylaminopropyl)carbodiimide and triethylamine in dimethylformamide, to obtain the compounds of formula (III) where Z represents a secondary amino group and where X, m, r and s have the meanings indicated for formula (I);

b) the compound of formula (III) obtained in stage a) above according to the protocol indicated in stage c) of the first above-mentioned method, is reacted to obtain the desired compounds of formula (I).

The invention also relates a third method of preparing the compounds of formula (I) in the formula of which R=CH$_3$, Y=Z=0 and X, m, n, r, s and R' have the meanings indicated for formula (I), characterized in that a 4-amino-3-methoxybenzoic acid is reacted with a 1-alkyl-4(hydroxyalky)piperidine in the presence of carbonyldiimidazole and potassium carbonate in tetrahydrofuran to obtain the desired compound of formula (I).

The invention also relates to a fourth method of preparing the compounds of formula (I) of which R=H and X, Y, Z, m, n, r, s, and R' have the same meanings as indicated for formula (I), characterized in that a compound of formula (I) in the formula of which R represents a methyl group is reacted with aluminum chloride in the presence of sodium iodide in acetonitrile to obtain the desired compound of formula (I).

The invention also relates to a fifth method of preparing the compounds of formula (I) in the formula of which R represents a straight- or branched-chain C1-C3 alkyl radical, capable of carrying one or more fluorine atoms, X, Y, Z, m, n, r, s, and R' having the meanings indicated for formula (I), characterized in that a compound of formula (I), wherein R=H and X, Y, Z, m, n, r, s, and R' having the meanings previously indicated for formula (I), is reacted with a halide or a straight- or branched-chain C1-C3 alkyl tosylate, capable of carrying one or more fluorine atoms, in the presence of potassium carbonate, in an appropriate solvent.

The invention also relates to a sixth process of preparing the compounds of formula (I) in the formula of which Y is a possible O-substituted oxime group, Z represents a methylene group capable of being substituted by a straight- or branched-chain C1-C3 alkyl group, X, m, n and R' being as indicated for formula (I), characterized in that a compound in formula (I) of which Z, X, m, n and R' have the meanings indicated above and Y=O, is reacted with an O-substituted hydroxylamine salt in the presence of calcium carbonate in an ethanol/water mixture, to obtain the desired compound of formula (I).

The invention also relates to a compound of formula (II) obtained at the end of stage a) of the first above-mentioned preparation method and a compound of formula (III) obtained at the end of stage b) of this same preparation method.

Lastly, the invention relates to a pharmaceutical composition, characterized in that it contains, as an active ingredient, at least one compound of formula (I).

According to a first aspect of the invention, the composition, which has just been defined, comprises a pharmaceutically acceptable excipient.

According to another aspect of the invention, the compound(s) of formula (I), that the composition contains, is (are) pharmaceutically acceptable.

According to another aspect of the invention, the composition contains at least one active ingredient having an inhibitory action of acetylcholinesterase and chosen from the group formed by:
a) 1,2,3,4-Tetrahydroacridin-9-amine
b) (RS)-2-[(1-benzyl-4-piperidyl)methyl-5,6-dimethoxy-2, 3-dihydroinden-1-one
c) (S)—N-ethyl-N-methyl-3-[(1-dimethylamino)ethyl]-phenyl carbamate and
d) 4aS,6R,8aS)-5,6,9,10,11,12-hexahydro-3-methoxy-11-methyl-4aH-[1]benzofuro[3a,3,2-ef][2]benzazepin-6-ol According to another aspect of the invention, the composition contains at least one partial 5-HT4 receptor agonist chosen from the group formed by:
a) 1-(4-amino-5-chloro-2-methoxyphenyl)-2-[1-butyl-4-piperidyl]propan-1 one,
b) N-(2-(4-(3-(4-amino-5-chloro-3-methoxyphenyl)-3-oxypropyl)piperidin-1-yl)ethyl)methane sulfonamide,
the said agonist being in a proportion of between 10/90 and 90/10 in relation to the active ingredient(s) formed by at least one compound of formula (I).

According to another aspect of the invention, the pharmaceutical composition is designed to be administered to mammals and has a promnesiant effect that can be used for the treatment of neurological diseases with amnestic deficit.

According to another aspect of the invention, the composition can be used for the treatment of Alzheimer's disease in a human subject.

According to another aspect of the invention, the composition can be used at active daily doses of formula (I) of between 1 and 20 mg/kg of body weight of the mammal to be treated, preferably 2 mg/kg.

According to another aspect of the invention, the composition is administered at doses of 10 to 1000 mg per day, the compounds of formula (I) preferably being administered at a rate of 0.2 to 2 mg once to five times a day.

According to another aspect of the invention, the composition is administered orally, chiefly in the form of tablets, capsules, microcapsules, powders, granules, syrups, solutions or suspensions taken by the oral or sublingual route or by the subcutaneous, intramuscular or intravenous route.

According to another aspect of the invention, the active ingredient is packaged in the form of a mixture with dispersion agents, softening agents, suspension agents, sweeteners or flavor enhancers.

According to another aspect of the invention, the composition is administered parenterally in the form of an aqueous suspension, saline solution, sterile solution or injectable solution.

BRIEF DESCRIPTION OF THE DRAWING

The FIGURE gives the results obtained on mice for the improvement of memory performance.

DETAILED DESCRIPTION

So as better to understand the subject matter of the invention and illustrate it in a non-limiting way, a certain number of examples will now be described. To facilitate identification of the different compounds illustrated in the examples, there now follows Table 1, corresponding to the compounds of formula (I), Table 2 corresponding to the compounds of formula (II) and Table 3 corresponding to the compounds of formula (III), each of these tables giving the meanings of the different substituents for each of the examples provided in the text below. The numbers appearing in these examples correspond to the compounds bearing the same numbers respectively in the above tables. Figures that appear in the text as superscripted, correspond to references used to implement the examples.

TABLE 1

Compounds of formula (I)

(I)

| Compound | X | Y | Z | m | n | r | s | R | R' |
|---|---|---|---|---|---|---|---|---|---|
| 1 | H | O | CH$_2$ | 1 | 1 | 1 | 1 | Me | n-propyl |
| 2 | Br | O | CH$_2$ | 1 | 1 | 1 | 1 | Me | n-propyl |
| 3 | I | O | CH$_2$ | 1 | 1 | 1 | 1 | Me | n-propyl |
| 4 | H | O | CH$_2$ | 1 | 1 | 1 | 1 | Me | cyclohexyl |
| 5 | F | O | CH$_2$ | 1 | 1 | 1 | 1 | Me | cyclohexyl |
| 6 | Cl | O | CH$_2$ | 1 | 1 | 1 | 1 | Me | cyclopropyl |
| 7 | Cl | O | CH$_2$ | 1 | 1 | 1 | 1 | Me | cyclobutyl |
| 8 | Cl | O | CH$_2$ | 1 | 1 | 1 | 1 | Me | cyclopentyl |
| 9 | Cl | O | CH$_2$ | 1 | 1 | 1 | 1 | Me | cyclohexyl |
| 10 | Cl | O | CHCH$_3$ | 1 | 1 | 1 | 1 | Me | cyclohexyl |
| 11 | Cl | O | CH$_2$ | 1 | 1 | 1 | 1 | Me | 2-methylcyclohexyl |
| 12 | Cl | O | CH$_2$ | 1 | 1 | 1 | 1 | Me | cylcoheptyl |
| 13 | Cl | O | CH$_2$ | 1 | 1 | 1 | 1 | Me | 4-piperidine |
| 14 | Br | O | CH$_2$ | 1 | 1 | 1 | 1 | Me | cyclohexyl |
| 15 | I | O | CH$_2$ | 1 | 1 | 1 | 1 | Me | cyclohexyl |
| 16 | Cl | O | CH$_2$ | 1 | 2 | 1 | 1 | Me | cyclohexyl |
| 17 | Cl | O | NH | 1 | 1 | 1 | 1 | Me | cyclohexyl |
| 18 | Br | O | NH | 1 | 1 | 1 | 1 | Me | cyclohexyl |
| 19 | I | O | NH | 1 | 1 | 1 | 1 | Me | cyclohexyl |
| 20 | Cl | O | O | 1 | 1 | 1 | 1 | Me | cylcohexyl |
| 21 | Cl | O | CH$_2$ | 1 | 1 | 1 | 1 | H | cyclohexyl |
| 22 | Cl | O | CH$_2$ | 1 | 1 | 1 | 1 | Et | cyclohexyl |
| 23 | Cl | O | CH$_2$ | 1 | 1 | 1 | 1 | F(CH$_2$)$_2$ | cyclohexyl |
| 24 | Cl | N— | CH$_2$ | 1 | 1 | 1 | 1 | Me | cyclohexyl |

TABLE 2

Compounds of Formula (II)

(II)

| Compound | X |
|---|---|
| 25 | H |
| 26 | F |
| 27 | Cl |
| 28 | Br |
| 29 | I |

TABLE 3

Compounds of Formula (III)

(III)

| Compound No | X | Z | m | r | s |
|---|---|---|---|---|---|
| 30 | H | CH₂ | 1 | 1 | 1 |
| 31 | Cl | CHCH3 | 1 | 1 | 1 |
| 32 | F | CH₂ | 1 | 1 | 1 |
| 33 | Br | CH₂ | 1 | 1 | 1 |
| 34 | I | CH₂ | 1 | 1 | 1 |
| 35 | Br | NH | 1 | 1 | 1 |
| 36 | I | NH | 1 | 1 | 1 |

References for implementing the examples:

[1] Eustache, F., Desgranges, B. Concepts et modèles en neuropsychologie de la mémoire. (2003). In Meulemans, T., Desgranges, B., Adam, S., Eustache, F. (eds.). Evaluation et prise en charge des troubles mnésiques. Marseille: Solal.

[1] Mingaud F., Mormede C., Etchamendy N., Mons N., Niedergang B., Wietrzych M., Pallet V., Jaffard R., Krezel W., Higueret P., Marighetto A., 2008 J. Neurosci. 28, 279-291.

[1] Levallet G, Hotte M, Boulouard M, Dauphin F (2009) Psychopharmacology (Berl). 202:125-39.

[1] Moser, P. C., Bergis, O. E., Jegham, S., Lochead, A., Duconseille, E., Terranova, J. P. J Pharmaco Exp Ther 2002; 302:731-741.

[1] Birks, J. Cochrane Database Syst. Rev. 2006, CD005593.

[1] Lezoualc'h, F. Exp. Neurol. 2007, 205, 325-329.

[1] Holzgrabe, U.; Kapkova, P.; Alptuzun, V.; Scheiber, J.; Kugelmann, E. Expert Opin. Ther. Targets 2007, 11, 161-179.

[1] Clark, R. D.; Eglen, R.; Jahangir, A.; Miller, A. B.; Gardner, J. O. PCT Int. Appl. 1994, WO9427965

[1] Sonda, S.; Kawahara, T.; Murozono, T.; Sato, N.; Asano, K.; Haga, K. Bioorg. Med. Chem. 2003, 11(19), 4225-4234

[1] Yang, W.; Ruan, Z.; Wang, Y.; Van Kirk, K.; Ma, Z.; Arey, B. J.; Cooper, C. B.; Seethala, R.; Feyen, J. H. M.; Dickson Jr, J. K. J. Med. Chem. 2009, 52 (4), 1204-1208

[1] Kaspi, J.; Lerman, O.; Arad, O.; Alnabari, M.; Sery, Y. Eur. Pat. Appl. 2004, 1386607

Example 1

1-(4-amino-2-methoxyphenyl)-3-[1-butyl-4-piperidyl]propan-1-one 1 ml of TFA is added to 184 mg of tert-butyl 4-[3-(4-amino-2-methoxy)-3-oxopropyl]piperidine-1-carboxylate (0.51 mmol) in solution in 1 ml of DCM. The reaction medium is stirred at AT for 15 minutes then concentrated in a rotary evaporator under reduced pressure. The residue is taken up in saturated NaHCO₃ then extracted 3 times with AcOEt. The organic phases are combined then washed in brine. The organic phase is then dried and concentrated to obtain 42 mg of deprotected product. This is directly engaged in the alkylation reaction by dissolving it in 3 ml of DMF to which is added 28 mg of K₂CO₃ (0.21 mmol) and 20 µL of iodobutane (0.18 mmol). The new reaction medium is held at 110° C. for 2 h. After dilution in AcOEt, the mixture is washed 4 times in brine, dried over MgSO₄ then concentrated. The residue obtained is purified over a silica gel column (DCM/AcOEt 10/0 to 0/10 then MeOH 5%). The product obtained has a yield of 22%.

$C_{19}H_{30}N_2O_2$

MP=80° C.

NMR $^1$H (CDCl₃): 0.89 (t, J=7.3 Hz, 3H, CH₃), 1.27 (m, 5H, 3 CH, CH$_{2\ BUT}$), 1.45 (m, 2H, CH$_{2\ BUT}$), 1.56 (m, 2H), 1.68 (m, 2H), 1.85 (m, 2H, 2 CHN), 2.27 (m, 2H, CH₂N), 2.90 (m, 4H, CH₂, 2 CHN), 3.83 (s, 3H, CH₃), 4.03 (s, 2H, NH₂), 6.13 (d, J=2.0 Hz, 1H, H$_{Ar}$), 6.24 (dd, J=8.7 Hz, J=2.0 Hz, 1H, H$_{Ar}$), 7.69 (d, J=8.7 Hz, 1H, H$_{Ar}$).

IR (KBr, cm$^{-1}$): 3438.2, 3255.4, 3228.4, 2952.1, 2926.8, 2932.8, 2856.9, 1726.5, 1640.7, 1594.1, 1468.1, 1434.3, 1272.4, 1259.8, 1212.6, 1177.1, 1030.2.

Example 2

1-(4-amino-5-bromo-2-methoxyphenyl)-3-[1-butyl-4-piperidyl]propan-1-one

Compound 3 is prepared according to the operating method of Example 1 described above, considering the following quantities:

tert-butyl 4-[3-(4-amino-5-bromo-2-methoxy)-3-oxopropyl]piperidine-1-carboxylate: 90 mg (0.19 mmol)

Trifluoroacetic acid: 1 ml

DCM: 1 ml iodobutane: 26 µL (0.23 mmol)

K₂CO₃: 34 mg (0.25 mmol)

DMF: 4 ml

The expected compound is obtained with a yield of 50% and is in the form of a pale yellow powder.

It has the following characteristics:

$C_{19}H_{29}BrN_2O_2$

MP=205° C.

NMR $^1$H (CDCl₃): 0.91 (t, J=7.3 Hz, 3H, CH₃), 1.29 (m, 5H, 3 CH, CH$_{2\ BUT}$), 1.48 (m, 2H, CH$_{2\ BUT}$), 1.58 (m, 2H), 1.70 (m, 2H), 1.89 (m, 2H, 2 CHN), 2.31 (m, 2H, CH₂N), 2.91 (m, 4H, CH$_2$, 2 CHN), 3.84 (s, 3H, CH$_3$), 4.55 (s, 2H, NH$_2$), 6.27 (s, 1H, H$_{Ar}$), 7.93 (s, 1H, H$_{Ar}$).

IR (KBr, cm$^{-1}$): 3436.2, 3255.8, 3156.4, 2961.4, 2932.8, 2873.5, 2633.0, 2516.0, 1725.7, 1655.3, 1619.3, 1584.6, 1461.4, 1417.0, 1300.1, 1253.4, 1216.2, 1179.2, 1044.2.

Example 3

1-(4-amino-5-iodo-2-methoxyphenyl)-3-[1-butyl-4-piperidyl]propan-1-one

Compound 4 is prepared according to the operating method of Example 1 described above, considering the following quantities:
tert-butyl 4-[3-(4-amino-5-iodo-2-methoxy)-3-oxopropyl]piperidine-1-carboxylate: 124 mg (0.25 mmol)
Trifluoroacetic acid: 1 ml
DCM: 1 ml
iodobutane: 28 µL (0.25 mmol)
K$_2$CO$_3$: 37 mg (0.27 mmol)
DMF: 4 ml The expected compound is obtained with a yield of 45% and is in the form of a pale yellow powder.
It has the following characteristics:
C$_{19}$H$_{29}$IN$_2$O$_2$
MP=130° C.
NMR $^1$H (CDCl$_3$): 0.91 (t, J=7.8 Hz, 3H, CH$_3$), 1.27 (m, 5H, 3 CH, CH$_{2\ BUT}$), 1.47 (m, 2H, CH$_{2\ BUT}$), 1.59 (m, 2H), 1.70 (m, 2H), 1.87 (m, 2H, 2 CHN), 2.29 (m, 2H, CH$_2$N), 2.91 (m, 4H, CH$_2$, 2 CHN), 3.84 (s, 3H, CH$_3$), 4.49 (s, 2H, NH$_2$), 6.25 (s, 1H, H$_{Ar}$), 8.11 (s, 1H, H$_{Ar}$).

IR (KBr, cm$^{-1}$): 3453.8, 3342.7, 3209.3, 2952.1, 2927.6, 2860.0, 1621.7, 1577.9, 1468.1, 1450.2, 1412.1, 1262.9, 1216.4, 1177.1, 1040.6.

Example 4

1-(4-amino-2-methoxyphenyl)-3-[1-(cyclohexylmethyl)-4-piperidyl]propan-1-one

Compound 1 is prepared according to the operating method of Example 1 described above, considering the following quantities:
tert-butyl 4-[3-(4-amino-2-methoxy)-3-oxopropyl]piperidine-1-carboxylate: 310 mg (0.86 mmol) Trifluoroacetic acid: 2 ml
DCM: 2 ml
(iodomethyl)cyclohexane: 87 µL (0.63 mmol)
K$_2$CO$_3$: 102 mg (0.74 mmol)
DMF: 5 ml The expected compound is obtained with a yield of 39% and is in the form of a yellow powder.
It has the following characteristics:
MP=90° C.
C$_{22}$H$_{34}$N$_2$O$_2$
NMR $^1$H (CDCl$_3$): 0.87 (m, 2H, 2 CH), 1.18 (m, 6H, 6 CH), 1.47 (m, 1H, CH), 1.64 (m, 7H, 5 CH, CH$_2$), 1.75 (m, 2H, 2 CH), 1.81 (m, 2H, 2 CHN), 2.08 (d, J=7.1 Hz, 2H, CH$_2$N), 2.85 (m, 2H, 2 CHN), 2.90 (m, 2H, CH$_2$), 3.82 (s, 3H, CH$_3$), 4.09 (s, 2H, NH$_2$), 6.16 (d, 1=2.0 Hz, 1H, H$_{Ar}$), 6.25 (dd, J=8.5 Hz, J=2.0 Hz, 1H, H$_{Ar}$), 7.70 (d, J=8.5 Hz, 1H, H$_{Ar}$).

IR (KBr, cm$^{-1}$): 3447.7, 3366.5, 3245.1, 2922.8, 2847.0, 2809.3, 2770.5, 1590.7, 1601.8, 1508.7, 468.1, 1448.3, 1429.4, 1347.3, 1310.9, 1272.3, 1257.2, 1218.0, 1206.9, 1134.0, 1122.8, 1031.4, 823.1.

Example 5

1-(4-amino-5-fluoro-2-methoxyphenyl)-3-[1-(cyclohexylmethyl)-4-piperidyl]propan-1-one 1 ml of TFA is added to 72 mg of tert-butyl 4-[3-(4-amino-5-fluoro-2-methoxy)-3-oxopropyl]piperidine-1-carboxylate (0.19 mmol) in solution in 1 ml of DCM. The reaction medium is stirred at AT for 15 minutes then concentrated in a rotary evaporator under reduced pressure. The residue is dissolved in 3 ml of DMF to which is added 262 mg of K$_2$CO$_3$ (1.89 mmol) and 35 µL of iodomethylcyclohexane (0.25 mmol). The new reaction medium is held at 110° C. for 3 h. After dilution in AcOEt, the mixture is washed 4 times in brine, dried over MgSO$_4$ then concentrated. The residue obtained is purified over a silica gel column (elution gradient: (DCM/AcOEt 10/0 to 0/10 then DCM+2% Et$_3$N). The expected product is obtained with a yield of 56%.
Appearance: yellow solid
MP=97° C.
C$_{22}$H$_{33}$FN$_2$O$_2$
NMR $^1$H (CDCl$_3$): 0.86 (m, 2H, 2 CH), 1.20 (m, 6H, 6 CH), 1.48 (m, 1H, CH), 1.64 (m, 7H, 5 CH, CH$_2$), 1.74 (m, 2H, 2 CH), 1.82 (m, 2H, 2 CHN), 2.08 (d, J=7.1 Hz, 2H, CH$_2$N), 2.85 (m, 2H, 2 CHN), 2.91 (m, 2H, CH$_2$), 3.84 (s, 3H, CH$_3$), 4.14 (s, 2H, NH$_2$), 6.27 (d, J$_{H-F}$=7.1 Hz, 1H, H$_{Ar}$), 7.55 (d, J$_{H-F}$=12.2 Hz, 1H, H$_{Ar}$).

IR (KBr, cm$^{-1}$): 3352.5, 3220.5, 2921.4, 2849.5, 2801.2, 2768.3, 1626.5, 1601.8, 1520.8, 1467.2, 1449.7, 1428.3, 1357.0, 1310.9, 1250.5, 1207.2, 1171.0, 1148.3, 1028.9, 823.8.

Example 6

1-(4-amino-5-chloro-2-methoxyphenyl)-3-[1-(cyclopropylmethyl)-4-piperidyl]propan-1-one Compound 6 is prepared according to the operating method of Example 5 described above, considering the following quantities:
tert-butyl 4-[3-(4-amino-5-chloro-2-methoxy-3-oxopropyl]piperidine-1-carboxylate:$^v$ 159 mg (0.40 mmol)
Trifluoroacetic acid: 2 ml
DCM: 2 ml
(iodomethyl)cyclopropane: 43 mg (0.48 mmol)
K$_2$CO$_3$: 553 mg (4.00 mmol)
DMF: 4 ml The expected compound is obtained with a yield of 39% and is in the form of a yellow powder.
MP=162° C.
C$_{19}$H$_{27}$ClN$_2$O$_2$
NMR $^1$H (CD$_3$OD): 0.18 (m, 2H), 0.58 (m, 2H), 0.94 (m, 1H), 1.34 (m, 3H), 1.61 (m, 2H), 1.79 (m, 2H), 2.10 (m, 2H), 2.33 (m, 2H), 2.95 (m, 2H), 3.15 (m, 2H), 3.89 (s, 3H, CH$_3$), 6.31 (s, 1H, H$_{Ar}$), 7.51 (s, 1H, H$_A$r).

IR (KBr, cm$^{-1}$): 3466.5, 3349.8, 2923.7, 2849.4, 2804.8, 2779.7, 1644.0, 1621.5, 1586.4, 1500.8, 1465.2, 1419.9, 1376.9, 1313.2, 1252.0, 1215.3, 1177.9, 1118.6, 825.7.

Example 7

1-(4-amino-5-chloro-2-methoxyphenyl)-3-[1-(cyclobutylmethyl)-4-piperidyl]propan-1-one Compound 7 is prepared according to the operating method of Example 5 described above, considering the following quantities:

tert-butyl 4-[3-(4-amino-5-chloro-2-methoxy)-3-oxopropyl]piperidine-1-carboxylate: 159 mg (0.40 mmol)
Trifluoroacetic acid: 2 ml
DCM: 2 ml
(iodomethyl)cyclobutane: 34 μL (0.30 mmol)
$K_2CO_3$: 45 mg (4.00 mmol)
DMF: 4 ml
The expected compound is obtained with a yield of 45% and is in the form of a yellow powder.
MP=143° C.
$C_{20}H_{29}ClN_2O_2$
NMR $^1$H (CDCl$_3$): 1.25 (m, 3H, 3 CH), 1.57 (m, 2H, CH$_2$), 1.78 (m, 8H, 4 CH$_{BUT}$, 2 CH, 2 CHN), 2.06 (m, 2H, 2 CH$_{BUT}$), 2.37 (d, J=6.6 Hz, 2H, CH$_2$N), 2.54 (m, 1H, CH$_{BUT}$), 2.83 (m, 2H, 2 CHN), 2.90 (m, 2H, CH$_2$), 3.85 (s, 3H, CH$_3$), 4.42 (s, 2H, NH$_2$), 6.25 (s, 1H, H$_{Ar}$), 7.78 (s, 1H, H$_{Ar}$).
IR (KBr, cm$^{-1}$): 3484.7, 3226.9, 2923.5, 2852.3, 2804.8, 2763.1, 1642.3, 1623.5, 1574.6, 1453.8, 1420.7, 1397.2, 1306.3, 1257.4, 1214.1, 1175.4, 1011.2, 830.4.

Example 8

1-(4-amino-5-chloro-2-methoxyphenyl)-3-[1-(cyclopentylmethyl)-4-piperidyl]propan-1-one Compound 8 is prepared according to the operating method of Example 1 described above, considering the following quantities:
tert-butyl 4-[3-(4-amino-5-chloro-2-methoxy)-3-oxopropyl]piperidine-1-carboxylate: 134 mg (0.34 mmol)
Trifluoroacetic acid: 2 ml
DCM: 2 ml
(iodomethyl)cyclopentane: 57 mg (0.27 mmol)
$K_2CO_3$: 41 mg (0.29 mmol)
DMF: 3 ml
The expected compound is obtained with a yield of 35% and is in the form of a yellow powder.
MP=142° C.
$C_{21}H_{31}ClN_2O_2$
NMR $^1$H (CDCl$_3$): 1.21 (m, 5H, 2 CH$_{PENT}$, 3 CH), 1.50 (m, 2H, 2 CH$_{PENT}$), 1.60 (m, 6H, 2 CH$_{PENT}$, CH$_2$, 2 CH), 1.76 (m, 2H, 2 CH$_{PENT}$), 1.86 (m, 2H, 2 CHN), 2.05 (m, 1H, CH$_{PENT}$), 2.24 (d, J=7.1 Hz, 2H, CH$_2$N), 2.90 (m, 4H, CH$_2$, 2 CHN), 3.85 (s, 3H, CH$_3$), 4.44 (s, 2H, NH$_2$), 6.26 (s, 1H, H$_{Ar}$), 7.79 (s, 1H, H$_{Ar}$).
IR (KBr, cm$^{-1}$): 3485.6, 3332.1, 2936.2, 2923.8, 2860.0, 2799.7, 2768.0, 1643.8, 1622.7, 1599.5, 1574.2, 1453.4, 1421.6, 1310.5, 1266.0, 1214.2, 1175.8, 1018.4, 831.0.

Example 9

1-(4-amino-5-chloro-2-methoxyphenyl)-3-[1-(cyclohexylmethyl)-4-piperidyl]propan-1-one Compound 9 is prepared according to the operating method of Example 1 described above, considering the following quantities:
tert-butyl 4-[3-(4-amino-2-methoxy)-3-oxopropyl]piperidine-1-carboxylate: 953 mg (2.41 mmol)
Trifluoroacetic acid: 2 ml
DCM: 2 ml
(bromomethyl)cyclohexane: 262 μL (1.88 mmol)
$K_2CO_3$: 281 mg (2.03 mmol)
DMF: 4 ml
The expected compound is obtained with a yield of 44% and is in the form of a pale yellow solid.

It has the following characteristics:
MP=154° C.
$C_{22}H_{33}ClN_2O_2$
NMR $^1$H (CDCl$_3$): 0.85 (m, 2H, 2 CH), 1.20 (m, 6H, 6 CH), 1.47 (m, 1H, CH), 1.68 (m, 11H, 7 CH, 2 CHN, CH$_2$), 2.08 (d, J=6.8 Hz, 2H, CH$_2$N), 2.84 (m, 2H, 2 CHN), 2.89 (m, 2H, CH$_2$), 3.85 (s, 3H, CH$_3$), 4.44 (s, 2H, NH$_2$), 6.26 (s, 1H, H$_{Ar}$), 7.79 (s, 1H, H$_{Ar}$).
IR (KBr, cm$^{-1}$): 3484.8, 3229.8, 2920.7, 2850.0, 2803.0, 2768.0, 1640.7, 1623.0, 1575.0, 1452.8, 1420.9, 1313.8, 1255.6, 1214.3, 1177.2, 1012.7, 831.0.

Example 10

1-(4-amino-5-chloro-2-methoxyphenyl)-3-[1-(cyclohexylmethyl)-4-piperidyl]-2 methylpropan-1-one Compound 10 is prepared according to the operating method of Example 5 described above, considering the following quantities:
tert-butyl 4-[3-(4-amino-5-chloro-2-methoxy)-2-methyl-3-oxopropyl]piperidine-1-carboxylate: 50 mg (0.12 mmol)
Trifluoroacetic acid: 5004
DCM: 2 ml
(bromomethyl)cyclohexane: 20 μL (0.15 mmol)
$K_2CO_3$: 168 mg (1.22 mmol)
DMF: 1 ml
The expected compound is obtained with a yield of 42% and is in the form of a yellow oil.
$C_{23}H_{35}ClN_2O_2$
NMR $^1$H (CDCl$_3$): 0.86 (m, 2H, 2 CH), 1.05 (d, J=6.8 Hz, 3H, CH$_3$), 1.19 (m, 6H, 6 CH), 1.49 (m, 1H, CH), 1.60 (m, 7H, 5 CH, CH$_2$), 1.73 (m, 2H, 2 CH), 1.86 (m, 2H, 2 CHN), 2.15 (d, J=6.6 Hz, 2H, CH$_2$N), 2.85 (m, 2H, 2 CHN), 3.57 (qd, 1=6.8 Hz, 1H, CH), 3.81 (s, 3H, CH$_3$), 4.42 (s, 2H, NH$_2$), 6.24 (s, 1H, H$_{Ar}$), 7.67 (s, 1H, H$_{Ar}$).
IR (KBr, cm$^{-1}$): 3477.5, 3351.5, 2922.4, 2851.8, 2801.6, 2766.2, 1650.4, 1621.4, 1590.8, 1464.5, 1450.3, 1417.3, 1305.1, 1255.8, 1214.8, 1178.2, 1007.6.

Example 11

1-(4-amino-5-chloro-2-methoxyphenyl)-3-[1-[(2-methylcyclohexyl)methyl]-4-piperidyl] propan-1-one Compound 11 is prepared according to the operating method of Example 5 described above, considering the following quantities:
tert-butyl 4-[3-(4-amino-5-chloro-2-methoxy)-3-oxopropyl]piperidine-1-carboxylate: 175 mg (0.44 mmol)
Trifluoroacetic acid: 1.5 ml
DCM: 3 ml
(iodomethyl)-2-methylcyclohexane: 127 mg (0.53 mmol)
$K_2CO_3$: 610 mg (4.42 mmol)
DMF: 4 ml
The expected compound is obtained with a yield of 45% and is in the form of a yellow solid.
MP=111° C.
$C_{23}H_{35}ClN_2O_2$
NMR $^1$H (CDCl$_3$): 0.83 (d, J=7.1 Hz, 3H, CH$_3$), 1.28 (m, 7H, 7 CH), 1.60 (m, 8H, 6 CH, CH$_2$), 1.66 (m, 2H, 2 CH), 1.86 (m, 2H, 2 CHN), 2.13 (d, J=6.8 Hz, 2H, CH$_2$N), 2.89 (m, 4H, CH$_2$, 2 CHN), 3.84 (s, 3H, CH$_3$), 4.49 (s, 2H, NH$_2$), 6.27 (s, 1H, H$_{Ar}$), 7.78 (s, 1H, H$_{Ar}$).

IR (KBr, cm$^{-1}$): 3482.4, 3336.7, 3209.3, 2921.4, 2850.5, 2803.8, 2771.2, 1640.7, 1618.5, 1585.3, 1466.1, 1453.4, 1421.6, 1310.5, 1253.4, 1215.0, 1180.3, 1018.4.

Example 12

1-(4-amino-5-chloro-2-methoxyphenyl)-3-[1-(cycloheptylmethyl)-4-piperidyl]propan-1-one Compound 12 is prepared according to the operating method of Example 5 described above, considering the following quantities:
tert-butyl 4-[3-(4-amino-5-chloro-2-methoxy)-3-oxopropyl]piperidine-1-carboxylate: 152 mg (0.38 mmol)
Trifluoroacetic acid: 1 ml
DCM: 2 ml
(iodomethyl)cycloheptane: 110 mg (0.46 mmol)
K$_2$CO$_3$: 535 mg (3.84 mmol)
DMF: 4 ml
The expected compound is obtained with a yield of 42% and is in the form of a yellow solid.
MP=148° C.
C$_{23}$H$_{35}$ClN$_2$O$_2$
NMR $^1$H (CDCl$_3$): 1.12 (m, 2H, 2 CH), 1.50 (m, 18H, CH$_2$, 16 CH), 1.95 (m, 2H, 2 CHN), 2.15 (m, 2H, CH$_2$N), 2.89 (m, 4H, CH$_2$, 2 CHN), 3.85 (s, 3H, CH$_3$), 4.49 (s, 2H, NH$_2$), 6.27 (s, 1H, H$_{Ar}$), 7.78 (s, 1H, H$_{Ar}$).
IR (KBr, cm$^{-1}$): 3481.0, 3247.7, 2919.6, 2850.2, 2800.8, 2768.1, 1637.6, 1621.7, 1582.3, 1453.6, 1419.5, 1307.1, 1252.8, 1214.4, 1176.1, 1012.6.

Example 13

1-(4-amino-5-chloro-2-methoxyphenyl)-3-[1-[(piperidin-4-yl)methyl]-4-piperidyl] propan-1-one dichlorohydrate The intermediate, resulting in compound 13, is prepared according to the operating method of Example 1 described above, considering the following quantities:
tert-butyl 4-[3-(4-amino-5-chloro-2-methoxy)-3-oxopropyl]piperidine-1-carboxylate: 212 mg (0.53 mmol)
Trifluoroacetic acid: 1 ml
DCM: 2 ml
tert-butyl 4-(iodomethyl)piperidine-1-carboxylate: 124 mg (0.38 mmol)
K$_2$CO$_3$: 62 mg (0.45 mmol)
DMF: 4 ml
This intermediate is obtained with a yield of 24% and is in the form of an oil.
40 mg of this intermediate (0.09 mmol) are then dissolved in 5 ml of EtOH to which 300 ml of concentrated HCl are added. After 3 hours of stirring at ambient temperature, the solution is concentrated in a rotary evaporator. Toluene is added to make an azeotropic mixture with the remaining residues of water. The dry residue obtained is then taken up in ethyl ether then filtered. 30 mg of expected product are then obtained with a yield of 80%
MP>260° C.
C$_{21}$H$_{34}$Cl$_3$N$_3$O$_2$
NMR $^1$H (DMSO-d6): 1.38 (m, 2H, 2 CH), 1.46 (m, 3H, CH, CH$_2$), 1.63 (m, 2H, 2 CH), 1.76 (m, 2H, 2 CH), 1.96 (m, 2H, 2 CH), 2.11 (m, 1H, CH), 2.81 (m, 6H, 4 CHN, CH$_2$), 2.91 (m, 2H, CH$_2$N), 3.22 (m, 2H, 2 CHN), 3.45 (m, 2H, 2 CHN), 3.79 (s, 3H, CH$_3$), 6.46 (s, 1H, H$_{Ar}$), 7.53 (s, 1H, H$_{Ar}$), 9.03 (m, 2H, 2 NH), 10.2 (m, 1H, NH).

IR (KBr, cm$^{-1}$): 3390.0, 3295.6, 3194.0, 2938.4, 2731.7, 1660.0, 1625.1, 1592.8, 1464.5, 1449.1, 1417.2, 1316.4, 1262.8, 1249.0, 1212.0, 1180.4.

Example 14

1-(4-amino-5-bromo-2-methoxyphenyl)-3-[1-(cyclohexylmethyl)-4-piperidyl]propan-1-one Compound 14 is prepared according to the operating method of Example 1 described above, considering the following quantities:
tert-butyl 4-[3-(4-amino-5-bromo-2-methoxy)-3-oxopropyl]piperidine-1-carboxylate: 65 mg (0.19 mmol)
Trifluoroacetic acid: 1 ml
DCM: 1 ml
(bromomethyl)cyclohexane: 32 μL (0.23 mmol)
K$_2$CO$_3$: 34 mg (0.25 mmol)
DMF: 4 ml
The expected compound is obtained with a yield of 60% and is in the form of a pale yellow powder.
MP=148° C.
C$_{22}$H$_{33}$BrN$_2$O$_2$
NMR $^1$H (CDCl$_3$): 0.87 (m, 2H, 2 CH), 1.20 (m, 6H, 6 CH), 1.48 (m, 1H, CH), 1.60 (m, 7H, 5 CH, CH$_2$), 1.74 (m, 2H, 2 CH), 1.81 (m, 2H, 2 CHN), 2.09 (d, J=6.8 Hz, 2H, CH$_2$N), 2.87 (m, 4H, 2 CHN, CH$_2$), 3.84 (s, 3H, CH$_3$), 4.51 (s, 2H, NH$_2$), 6.26 (s, 1H, H$_{Ar}$), 7.93 (s, 1H, H$_{Ar}$).
IR (KBr, cm$^{-1}$): 3471.6, 3224.0, 2920.9, 2851.8, 2801.6, 2766.2, 1634.4, 1621.5, 1580.7, 1449.7, 1417.3, 1302.3, 1260.8, 1216.5, 1178.2, 1042.4.

Example 15

1-(4-amino-5-iodo-2-methoxyphenyl)-3-[1-(cyclohexylmethyl)-4-piperidyl]propan-1-one Compound 12 is prepared according to the operating method of Example 1 described above, considering the following quantities:
tert-butyl 4-[3-(4-amino-5-iodo-2-methoxy)-3-oxopropyl]piperidine-1-carboxylate: 110 mg (0.23 mmol)
Trifluoroacetic acid: 2 ml
DCM: 2 ml
(bromomethyl)cyclohexane: 36 μL (0.26 mmol)
K$_2$CO$_3$: 33 mg (0.24 mmol)
DMF: 2 ml
The expected compound is obtained with a yield of 42% and is in the form of a yellow powder.
It has the following characteristics:
MP=178-180° C.
C$_{22}$H$_{33}$IN$_2$O$_2$
NMR $^1$H (CDCl$_3$): 0.85 (m, 2H, 2 CH), 1.20 (m, 6H, 6 CH), 1.47 (m, 1H, CH), 1.69 (m, 11H, 7 CH, 2 CHN, 1 CH$_2$), 2.07 (d, J=7.1 Hz, 2H, CH$_2$N), 2.84 (m, 2H, 2 CHN), 2.88 (m, 2H, CH$_2$), 3.84 (s, 3H, CH$_3$), 4.49 (s, 2H, NH$_2$), 6.25 (s, 1H, H$_{Ar}$), 8.11 (s, 1H, H$_{Ar}$).
IR (KBr, cm$^{-1}$): 3323.7, 3212.5, 2919.4, 2847.4, 2799.7, 2768.1, 1634.4, 1624.9, 1574.7, 1448.8, 1412.1, 1262.9, 1215.3, 1177.1, 1040.6, 834.2.

Example 16

1-(4-amino-5-chloro-2-methoxyphenyl)-3-[1-(cyclohexylethyl)-4-piperidyl]propan-1-one Compound 16 is prepared according to the operating method of Example 5 described above, considering the following quantities:

tert-butyl 4-[3-(4-amino-5-chloro-2-methoxy)-3-oxopropyl]piperidine-1-carboxylate: 145 mg (0.37 mmol)
Trifluoroacetic acid: 2 ml
DCM: 2 ml
(iodoethyl)cyclohexane: 140 mg (0.44 mmol)
$K_2CO_3$: 506 mg (3.66 mmol)
DMF: 5 ml
The expected compound is obtained with a yield of 40% and is in the form of a yellow powder.
It has the following characteristics:
MP=170° C.
$C_{23}H_{35}ClN_2O_2$
NMR $^1$H (CDCl$_3$): 0.90 (m, 2H, 2 CH), 1.20 (m, 7H, 7 CH), 1.36 (m, 2H, CH$_2$), 1.61 (m, 9H, 7 CH, CH$_2$), 1.83 (m, 2H, 2 CHN), 2.28 (m, 2H, CH$_2$N), 2.89 (m, 4H, 2 CHN, CH$_2$), 3.82 (s, 3H, CH$_3$), 4.42 (s, 2H, NH$_2$), 6.23 (s, 1H, H$_{Ar}$), 7.76 (s, 1H, H$_{Ar}$).
IR (KBr, cm$^{-1}$): 3480.5, 2921.3, 2851.8, 1639.6, 1624.0, 1575.6, 1453.0, 1420.3, 1383.6, 1306.2, 1256.9, 1213.7, 1174.9, 1022.2, 830.2.

Example 17

4-amino-5-chloro-[[1-(cyclohexylmethyl)-4-piperidyl]methyl]-2-methoxybenzamide

Compound 17 is prepared according to the operating method of Example 5 described above, considering the following quantities:
tert-butyl 4-[[(4-amino-5-chloro-2-methoxy-benzoyl)amino]methyl]piperidine-1-carboxylate:$^{vi}$ 66 mg (0.17 mmol)
Trifluoroacetic acid: 1 ml
DCM: 2 ml
(bromomethyl)cyclohexane: 39 mg (0.22 mmol)
$K_2CO_3$: 232 mg (1.68 mmol)
DMF: 3 ml
The expected compound is obtained with a yield of 38% and is in the form of a yellow solid.
It has the following characteristics:
MP=154-155° C.
$C_{21}H_{32}ClN_3O_2$
NMR $^1$H (CDCl$_3$): 0.90 (m, 2H, 2 CH), 1.16 (m, 4H, 4 CH), 1.34 (m, 2H, 2 CH), 1.47 (m, 1H, CH), 1.68 (m, 7H, 7 CH), 1.88 (m, 2H, 2 CHN), 2.11 (d, J=7.1 Hz, 2H, CH$_2$N), 2.89 (m, 2H, 2 CHN), 3.29 (m, 2H, CH$_2$N), 3.88 (s, 3H, CH$_3$), 4.35 (s, 2H, NH$_2$), 6.27 (s, 1H, H$_{Ar}$), 7.73 (t, J=5.2 Hz, 1H, NH), 8.03 (s, 1H, H$_{Ar}$).
IR (KBr, cm$^{-1}$): 3399.9, 2925.1, 2853.7, 1621.7, 1593.0, 1536.1, 1497.9, 1453.4, 1418.5, 1313.7, 1256.5, 1212.0, 1145.4, 989.8, 729.5.

Example 18

4-amino-5-bromo-N-[[1-(cyclohexylmethyl)-4-piperidyl]methyl]-2-methoxybenzamide

Compound 18 is prepared according to the operating method of Example 1 described above, considering the following quantities:
tert-butyl 4-[[(4-amino-5-bromo-2-methoxy-benzoyl)amino]methyl]piperidine-1-carboxylate: 250 mg (0.56 mmol)
Trifluoroacetic acid: 4 ml
DCM: 4 ml
(bromomethyl)cyclohexane: 68 µL (0.72 mmol)
$K_2CO_3$: 92 mg (0.66 mmol)
DMF: 6 ml
MP=162° C.
$C_{21}H_{32}BrN_3O_2$
NMR $^1$H (CD$_3$OD): 0.93 (m, 2H), 1.23 (m, 5H), 1.41 (m, 2H), 1.61 (m, 1H), 1.70 (m, 8H), 2.21 (m, 2H), 2.36 (m, 2H), 3.09 (m, 2H), 3.90 (s, 3H, CH$_3$), 6.27 (s, 1H, H$_{Ar}$), 7.94 (s, 1H, H$_{Ar}$).
IR (KBr, cm$^{-1}$): 3450.5, 3406.0, 3319.5, 3195.6, 2918.3, 2847.5, 2763.4, 2417.3, 1634.8, 1593.8, 1543.1, 1496.2, 1463.1, 1448.0, 1309.8, 1255.6, 1210.2, 1179.1, 1134.8, 1041.2, 979.1, 838.9.

Example 19

4-amino-5-iodo-N-[[1-(cyclohexylmethyl)-4-piperidyl]methyl]-2-methoxybenzamide

Compound 19 is prepared according to the operating method of Example 5 described above, considering the following quantities:
tert-butyl 4-[[(4-amino-5-iodo-2-methoxy-benzoyl)amino]methyl]piperidine-1-carboxylate: 138 mg (0.28 mmol)
Trifluoroacetic acid: 1 ml
DCM: 2 ml
(bromomethyl)cyclohexane: 60 mg (0.34 mmol)
$K_2CO_3$: 390 mg (2.82 mmol)
DMF: 3 ml
The expected compound is obtained with a yield of 40% and is in the form of a yellow powder.
It has the following characteristics:
MP=174° C.
$C_{21}H_{32}IN_3O_2$
NMR $^1$H (CDCl$_3$): 0.85 (m, 2H, 2 CH), 1.20 (m, 4H, 4 CH), 1.34 (m, 2H, 2 CH), 1.47 (m, 1H, CH), 1.67 (m, 7H, 7 CH), 1.86 (m, 2H, 2 CHN), 2.10 (d, J=7.1 Hz, 2H, CH$_2$N), 2.88 (m, 2H, 2 CHN), 3.31 (m, 2H, CH$_2$N), 3.90 (s, 3H, CH$_3$), 4.40 (s, 2H, NH$_2$), 6.27 (s, 1H, H$_{Ar}$), 7.69 (t, J=4.8 Hz, 1H, NH), 8.45 (s, 1H, H$_{Ar}$).
IR (KBr, cm$^{-1}$): 3451.5, 3407.6, 3313.5, 3196.4, 2916.7, 2845.4, 2792.0, 1636.2, 1582.8, 1551.4, 1490.2, 1446.1, 1408.6, 1302.1, 1267.0, 1211.3, 1182.3, 1143.0, 1043.1, 977.6, 836.4.

Example 20

[1-(cyclohexylmethyl)-4-piperidyl]methyl 4-amino-5-chloro-2-methoxybenzoate

Under N$_2$, 89 mg of CDI (0.55 mmol) are added to a suspension of 101 mg of 4-amino-5-chloro-2-methoxybenzoic acid (0.50 mmol) in 3 ml of freshly distilled THF. The reaction medium is stirred at ambient temperature for 24 h then a solution of 106 mg of (1-(cyclohexylmethyl)piperidin-4-yl)methanol (0.50 mmol) in 2 ml of freshly distilled THF then 21 mg of NaH (0.55 mmol). After stirring at AT over a weekend, the THF is evaporated. The residue obtained is taken up in AcOEt, washed in water then dried over MgSO$_4$. After concentration, the reaction crude is purified over a silica gel column (elution gradient: 100% DCM to 100% AcOEt) to obtain the expected product with a yield of 31%.
Appearance: creamy white solid
MP=129° C.
$C_{21}H_{31}ClN_2O_3$
NMR $^1$H (CDCl$_3$): 0.86 (m, 2H, 2 CH), 1.19 (m, 4H, 4 CH), 1.39 (m, 2H, 2 CH), 1.48 (m, 1H, CH), 1.69 (m, 7H, 7 CH), 1.86 (m, 2H, 2 CHN), 2.10 (d, J=7.1 Hz, 2H, CH$_2$N), 2.88 (m, 2H, 2 CHN), 3.84 (s, 3H, CH$_3$), 4.08 (d, J=6.0 Hz, 2H, CH$_2$O), 4.45 (s, 2H, NH$_2$), 6.29 (s, 1H, H$_{Ar}$), 7.81 (s, 1H, H$_{Ar}$).

IR (KBr, cm$^{-1}$): 3472.9, 3329.8, 2919.7, 2850.5, 1694.9, 1621.3, 1600.1, 1449.3, 1316.9, 1275.6, 1234.3, 1109.2, 1072.4, 1053.3, 983.4.

Example 21

1-(4-amino-5-chloro-2-hydroxyphenyl)-3-[1-(cyclo-hexylmethyl)-4-piperidyl]propan-1-one 72 mg of AlCl$_3$ (0.54 mmol) and 81 mg of NaI (0.54 mmol) are added to a solution of 140 mg of 1-(4-amino-5-chloro-2-methoxyphenyl)-3-[1-(cyclohexylmethyl)-4-piperidyl]propan-1-one (Example 6, 0.36 mmol) in 10 ml of CH$_3$CN. The reaction medium is then heated at reflux for 4 h. After dilution with DCM, the organic phase is washed in water then saturated NaHCO$_3$. After drying over MgSO$_4$, filtration and concentration, the residue is purified over silica gel (elution gradient: DCM to DCM/MeOH (9/1)) to obtain 109 mg of 1-(4-amino-5-chloro-2-hydroxyphenyl)-3-[1-(cyclohexylmethyl)-4-piperidyl]propan-1-one with a yield of 81%.

Appearance: pale yellow solid
MP=124° C.
C$_{21}$H$_{31}$ClN$_2$O$_2$
NMR $^1$H (CDCl$_3$): 0.86 (m, 2H, 2 CH), 1.22 (m, 6H, 6 CH), 1.48 (m, 1H, CH), 1.71 (m, 9H, 7 CH, CH$_2$), 1.85 (m, 2H, 2 CHN), 2.10 (d, J=6.8 Hz, 2H, CH$_2$N), 2.85 (m, 4H, CH$_2$, 2 CHN), 4.65 (s, 2H, NH$_2$), 6.23 (s, 1H, H$_{Ar}$), 7.61 (s, 1H, H$_{Ar}$), 12.72 (s, 1H, OH).

IR (KBr, cm$^{-1}$): 3471.8, 3368.2, 2920.9, 2849.0, 2800.3, 2766.4, 1636.8, 1521.4, 1505.8, 1448.7, 1424.0, 1379.3, 1352.3, 1320.5, 1270.7, 1230.6, 1212.4, 1112.0, 812.5.

Example 22

1-(4-amino-5-chloro-2-éthoxyphenyl)-3-[1-(cyclo-hexylmethyl)-4-piperidyl]propan-1-one 27 mg of K$_2$CO$_3$ (0.20 mmol) and 8.54 of iodoethane (0.11 mmol) are added to a solution of 37 mg of 1-(4-amino-5-chloro-2-hydroxyphenyl)-3-[1-(cyclohexylmethyl)-4-piperidyl]propan-1-one (0.10 mmol) in 2 ml of DMF. The reaction medium is stirred for 2 h 30 at 110° C. The solution is then diluted with AcOEt then washed 4 times with a saturated NaCl solution. The organic phase is then dried over MgSO$_4$, filtered and concentrated. The residue obtained is then purified over silica gel (preparation: DCM+2% Et$_3$N; elution: DCM (9/1)) to obtain 33 mg of expected product (yield=84%) in the form of a white solid.

MP=147° C.
C$_{23}$H$_{35}$ClN$_2$O$_2$
NMR $^1$H (CDCl$_3$): 0.81 (m, 2H, 2 CH), 1.20 (m, 6H, 6 CH), 1.44 (t, J=7.1 Hz, 3H, CH$_3$), 1.47 (m, 1H, CH), 1.68 (m, 11H, 7 CH, 2 CHN, CH$_2$), 2.05 (d, l=6.8 Hz, 2H, CH$_2$N), 2.82 (m, 2H, 2 CHN), 2.92 (t, J=6.8 Hz, 2H, CH$_2$), 4.03 (qd, J=7.1 Hz, 2H, CH$_2$O), 4.39 (s, 2H, NH$_2$), 6.21 (s, 1H, H$_{Ar}$), 7.76 (s, 1H, H$_{Ar}$).

IR (KBr, cm$^{-1}$): 3441.1, 3214.2, 2926.3, 2853.7, 1651.8, 1621.7, 1586.1, 1501.8, 1434.3, 1383.5, 1307.3, 1259.7, 1205.7, 1132.7, 1028.4, 802.5.

Example 23

1-[4-amino-5-chloro-2-(2-fluoroéthoxy)phenyl]-3-[1-(cyclohexylmethyl)-4-piperidyl]propan-1-one Compound 23 is prepared according to the operating method of Example 22 described above, considering the following quantities:
1-(4-amino-5-chloro-2-hydroxyphenyl)-3-[1-(cyclohexylmethyl)-4-piperidyl]propan-1-one: 44 mg (0.12 mmol)
2-fluoroethyl tosylate: 28 mg (0.13 mmol)
K$_2$CO$_3$: 32 mg (0.23 mmol)
DMF: 3 ml
The expected compound is obtained with a yield of 86% and is in the form of a white solid.
It has the following characteristics:
MP=144-146° C.
C$_{23}$H$_{34}$ClFN$_2$O$_2$
NMR $^1$H (CDCl$_3$): 0.82 (m, 2H, 2 CH), 1.18 (m, 6H, 6 CH), 1.44 (m, 1H, CH), 1.66 (m, 11H, 7 CH, CH$_2$, 2 CHN), 2.05 (d, J=7.1 Hz, 2H, CH$_2$N), 2.81 (m, 2H, 2 CHN), 2.94 (m, 2H, CH$_2$), 4.17 (m, &H, CH), 4.24 (m, 1H, CH), 4.43 (s, 2H, NH$_2$), 4.69 (m, 1H, CH), 4.82 (m, 1H, CH), 6.20 (s, 1H, H$_{Ar}$), 7.78 (s, 1H, H$_{Ar}$).

IR (KBr, cm$^{-1}$): 3431.6, 3266.5, 2926.7, 2853.7, 2675.9, 1644.3, 1618.5, 1586.8, 1501.0, 1450.2, 1434.3, 1383.5, 1342.3, 1310.5, 1256.5, 1205.7, 1183.5, 1164.4, 1072.4, 1047.3, 1018.4, 812.0.

Example 24

2-chloro-4-[[2-[1-(cyclohexylmethyl)-4-piperidyl]ethyl]-N-methoxycarbonimidoyl]-5-methoxyaniline 69 mg of methoxyamine hydrochloride (0.82 mmol) are added to a solution of 90 mg of 1-(4-amino-5-chloro-2-methoxyphenyl)-3-[1-(cyclohexylmethyl)-4-piperidyl]propan-1-one (0.23 mmol) in 2 ml of pyridine. The reaction medium is stirred at ambient temperature for 24 h.

After dilution in water, the aqueous phase is extracted 3 times with AcOEt. The organic phases are combined then washed 5 times in brine, dried over MgSO$_4$ then concentrated. The residue is purified over silica gel (preparation: DCM+2% Et$_3$N; elution gradient DCM/AcOEt: 10/0 to 9/1) to obtain 41 mg of expected product (stereoisomer E) in the form of a pale yellow oil (yield=42%).

C$_{23}$H$_{36}$C1N$_3$O$_2$
NMR $^1$H (CDCl$_3$): 0.83 (m, 2H, 2 CH), 1.22 (m, 8H, 6 CH, CH$_2$), 1.44 (m, 1H, CH), 1.65 (m, 9H, 7 CH, 2 CHN), 2.04 (d, J=6.8 Hz, 2H, CH$_2$N), 2.63 (m, 2H, CH$_2$), 2.79 (m, 2H, 2 CHN), 3.72 (s, 3H, CH$_3$), 3.89 (s, 3H, CH$_3$), 4.09 (s, 2H, NH$_2$), 6.25 (s, 1H, H$_{Ar}$), 7.12 (s, 1H, H$_{Ar}$).

IR (KBr, cm$^{-1}$): 3475.2, 3385.4, 2921.3, 2849.7, 2800.7, 2766.8, 1621.2, 1506.2, 1463.8, 1450.4, 1411.0, 1337.9, 1257.8, 1212.9, 1176.3, 1051.6, 984.8, 877.6.

Example 25[vii]

Ethyl 3-(2-methoxy-4-methylphenyl)-3-oxopropanoate 320 mg of CDI (1.98 mmol) are carefully added to a suspension of 300 mg of 4-amino-2-methoxybenzoic (1.78 mmol) acid in 15 ml of distilled THF. The mixture is stirred at ambient temperature for 4 h. 336 mg of 3-ethoxy-3-oxopropanoate potassium salt (2.16 mmol) and 205 mg of MgCl$_2$ (2.16 mmol) are then added per portion. The reaction mixture is stirred at ambient temperature for 2 days. After extending with 30 ml of Et$_2$O, the solution is then washed with water, a saturated solution of NaHCO$_3$ and a saturated solution of NaCl. After drying over MgSO$_4$, the organic phase is evaporated and the crude product is purified over silica gel (elution gradient: DCM to DCM/AcOEt 95/5) to give 194 mg of ethyl 3-(4-amino-2-methoxyphenyl)-3-oxopropanoate with a yield of 46%.

Appearance: colorless oil
C$_{12}$H$_{15}$NO$_4$
NMR $^1$H (CDCl$_3$): 1.24 (t, J=7.8 Hz, 3H, CH$_3$), 3.82 (s, 3H, CH$_3$), 3.88 (s, 2H, CH$_2$), 4.17 (q, J=7.8 Hz, 2H, CH$_2$), 4.18 (s, 2H, NH$_2$), 6.12 (d, J=2.1 Hz, 1H, H$_{Ar}$), 6.27 (dd, J=8.8 Hz, J=2.1 Hz, 1H, H$_{Ar}$), 7.83 (d, J=8.8 Hz, 1H, H$_{Ar}$).
IR (KBr, cm$^{-1}$): 3460.2, 3365.2, 3228.0, 2980.7, 1729.3, 1640.7, 1592.1, 1471.0, 1433.6, 1322.6, 1253.2, 1215.2, 1129.9, 1026.2, 830.3.

Example 26[10]

Ethyl 3-(4-amino-5-chloro-2-methoxy-phenyl)-3-oxopropanoate 533 mg of CDI (3.29 mmol) are carefully added to a suspension of 603 mg of 4-amino-5-chloro-2-methoxybenzoic acid (2.99 mmol) in 30 ml of distilled THF.[10] The mixture is stirred at ambient temperature for 6 h. Then, 611 mg of 3-ethoxy-3-oxopropanoate potassium salt (3.59 mmol) and 342 mg of MgCl$_2$ (3.59 mmol) are added per portion. The reaction mixture is stirred at 40° C. for 2 days. After extending with 30 ml of Et$_2$O, the solution is then washed with water, a saturated solution of NaHCO$_3$ and a saturated solution of NaCl. After drying over MgSO$_4$, the organic phase is evaporated and the crude product is purified over silica gel (gradient elution: CH/AcOEt 8/2 to 7/3) to give 507 mg of ethyl 3-(4-amino-5-chloro-2-methoxyphenyl)-3-oxopropanoate with a yield of 62%.

Appearance: white solid
MP=124° C.
C$_{12}$H$_{14}$ClNO$_4$
NMR $^1$H (CDCl$_3$): 1.24 (t, J=7.3 Hz, 3H, CH$_3$), 3.82 (s, 3H, CH$_3$), 3.87 (s, 2H, CH$_2$), 4.17 (q, J=7.3 Hz, 2H, CH$_2$), 4.56 (s, 2H, NH$_2$), 6.23 (s, 1H, H$_{Ar}$), 7.92 (s, 1H, H$_{Ar}$).
IR (KBr, cm$^{-1}$): 3463.0, 3362.5, 3222.9, 2982.6, 1725.0, 1647.9, 1621.7, 1572.8, 1468.9, 1456.6, 1422.8, 1325.5, 1261.6, 1221.0, 1155.4, 1024.0, 836.8.

Example 27

Ethyl 3-(4-amino-5-fluoro-2-methoxy-phenyl)-3-oxopropanoate

Compound 27 is prepared according to the operating method of Example 26 described above, considering the following quantities:
4-amino-5-fluoro-2-methoxybenzoic acid: 272 mg (1.47 mmol)
CDI: 262 mg (1.62 mmol)
3-ethoxy-3-oxopropanoate potassium salt: 300 mg (1.76 mmol)
MgCl$_2$: 168 mg (1.76 mmol)
THF: 30 ml
The expected compound is obtained with a yield of 65% and is in the form of a white solid.
MP=83-85° C.
C$_{12}$H$_{14}$FNO$_4$
NMR $^1$H (CDCl$_3$): 1.24 (t, J=7.1 Hz, 3H, CH$_3$), 3.82 (s, 3H, CH$_3$), 3.88 (s, 2H, CH$_2$), 4.17 (q, J=7.1 Hz, 2H, CH$_2$), 4.26 (s, 2H, NH$_2$), 6.24 (d, J=7.1 Hz, 1H, H$_{Ar}$), 7.65 (d, J=11.9 Hz, 1H, H$_{Ar}$).
IR (KBr, cm$^{-1}$): 3469.7, 3464.2, 3231.6, 2981.7, 1729.6, 1652.9, 1628.0, 1604.2, 1522.4, 1469.6, 1431.7, 1366.9, 1319.2, 1250.2, 1211.3, 1189.8, 1139.2, 1026.3, 829.9.

Example 28

Ethyl 3-(4-amino-5-bromo-2-methoxy-phenyl)-3-oxopropanoate

Compound 28 is prepared according to the operating method of Example 26 described above, considering the following quantities:
4-amino-5-bromo-2-methoxybenzoic acid: 500 mg (2.03 mmol)
CDI: 362 mg (2.23 mmol)
3-ethoxy-3-oxopropanoate potassium salt: 414 mg (2.44 mmol)
MgCl$_2$: 232 mg (2.44 mmol)
THF: 30 ml
The expected compound is obtained with a yield of 50% and is in the form of a white powder.
It has the following characteristics:
MP=128° C.
C$_{12}$H$_{14}$BrNO$_4$
NMR $^1$H (CDCl$_3$): 1.24 (t, J=7.8 Hz, 3H, CH$_3$), 3.83 (s, 3H, CH$_3$), 3.87 (s, 2H, CH$_2$), 4.18 (q, J=7.8 Hz, 2H, CH$_2$), 4.59 (s, 2H, NH$_2$), 6.23 (s, 1H, H$_{Ar}$), 8.08 (s, 1H, H$_{Ar}$).
IR (KBr, cm$^{-1}$): 3456.3, 3358.0, 3217.6, 2981.0, 1724.9, 1647.4, 1620.4, 1578.0, 1468.2, 1454.3, 1420.4, 1321.5, 1265.7, 1221.2, 1153.7, 1023.7, 835.0.

Example 29

Ethyl 3-(4-amino-5-iodo-2-methoxy-phenyl)-3-oxopropanoate

Compound 29 is prepared according to the operating method of Example 26 described above, considering the following quantities:
4-amino-5-iodo-2-methoxybenzoic acid: 355 mg (1.21 mmol)
CDI: 216 mg (1.33 mmol)
3-ethoxy-3-oxopropanoate potassium salt: 247 mg (1.45 mmol)
MgCl$_2$: 138 mg (1.45 mmol)
THF: 30 ml
The expected compound is obtained with a yield of 50% and is in the form of a white powder.
It has the following characteristics:
MP=140° C.
C$_{12}$H$_{14}$INO$_4$
NMR $^1$H (CDCl$_3$): 1.24 (t, J=7.8 Hz, 3H, CH$_3$), 3.82 (s, 3H, CH$_3$), 3.87 (s, 2H, CH$_2$), 4.17 (q, J=7.8 Hz, 2H, CH$_2$), 4.65 (s, 2H, NH$_2$), 6.22 (s, 1H, H$_{Ar}$), 8.25 (s, 1H, H$_{Ar}$).
IR (KBr, cm$^{-1}$): 3454.0, 3350.0, 3212.1, 2976.2, 1732.2, 1645.6, 1619.0, 1569.6, 1467.0, 1454.5, 1421.4, 1325.2, 1264.7, 1225.9, 1190.5, 1153.4, 1031.9, 831.2.

Example 30[viii]

Tert-butyl 4-[3-(4-amino-2-methoxyphenyl)-3-oxopropyl]piperidine-1-carboxylate 437 mg of K$_2$CO$_3$ (3.16 mmol) and 617 mg of tert-butyl 4-(iodomethyl)piperidine-1-carboxylate (1.89 mmol) are added to a solution of 379 mg of the compound of Example 22 (1.58 mmol) in 30 ml of DMF. The reaction mixture is stirred at ambient temperature for 1 week. After dilution in water, the product is extracted with Et$_2$O (3×40 ml). The organic phases are combined washed 3 times with water and once with brine then dried over MgSO$_4$. After concentration, the residue is dissolved in 10 ml of a binary mixture EtOH/H$_2$O (5/1) to which 407 mg of KOH (7.27 mmol) are added. The new reaction medium is then heated at reflux for 4 hours. The EtOH is removed in a rotary evaporator then the resulting aqueous phase is diluted with water, extracted with DCM. The organic phases are combined, washed with water and brine, dried over MgSO$_4$ then concentrated. The crude product is purified over silica gel (elution gradient: DCM to DCM/AcOEt 6/4) to obtain 469 mg of tert-butyl 4-[3-(4-amino-2-methoxy)-3-oxopropyl]piperidine-1-carboxylate with a yield of 82%.

Appearance: yellow oil $C_{20}H_{30}N_2O_4$

NMR $^1$H (CDCl$_3$): 1.11 (m, 2H, 2 CH), 1.45 (m, 10H, 3 CH$_3$, CH), 1.61 (m, 2H, CH$_2$), 1.68 (m, 2H, 2 CH), 2.67 (m, 2H, 2 CHN), 2.90 (m, 2H, CH$_2$), 3.86 (s, 3H, CH$_3$), 4.07 (m, 2H, 2 CHN), 4.62 (s, 2H, NH$_2$), 6.16 (d, J=2.0 Hz, 1H, H$_{Ar}$), 6.27 (dd, J=8.6 Hz, J=2.0 Hz, 1H, H$_{Ar}$), 7.71 (d, J=8.6 Hz, 1H, H$_{Ar}$).

IR (KBr, cm$^{-1}$): 3442.8, 3355.8, 3240.2, 2974.2, 2930.5, 2851.3, 1675.9, 1642.3, 1595.9, 1468.4, 1431.1, 1365.6, 1277.7, 1212.9, 1162.6.

Example 31

Tert-butyl 4-[3-(4-amino-5-chloro-2-methoxyphenyl)-2-methyl-3-oxopropyl]piperidine-1-carboxylate Under N$_2$, at −10° C., 909 µL of LIHMDS 1M in THF (0.909 mmol) are added to a solution of 300 mg of tert-butyl 4-[3-(4-amino-5-chloro-2-methoxyphenyl)-2-methyl-3-oxopropyl]piperidine-1-carboxylate (0.76 mmol) in 3 ml of freshly distilled THF. The reaction medium is stirred for 15 minutes at −10° C. then 57 ml of iodomethane (0.909 mmol) are added. After 3 h and a slow return to AT, the solution is concentrated under reduced pressure. The residue is taken up in AcOEt and washed twice with water. The organic phase is dried over MgSO$_4$ then concentrated. The crude product is purified over silica gel (elution gradient: DCM to DCM/AcOEt 95/5) to obtain 76 mg of expected product (yield=25%).

Appearance: pale yellow oil $C_{21}H_{31}ClN_2O_4$

NMR $^1$H (CDCl$_3$): 1.00 (m, 2H, 2 CH), 1.06 (d, J=7.1 Hz, 3H, CH$_3$) 1.18 (m, 1H, 1 CH), 1.46 (m, 10H, 3 CH$_3$, CH), 1.55 (m, 2H, 2 CH), 1.68 (m, 1H, 1 CH), 2.62 (m, 2H, 2 CHN), 2.90 (m, 2H, 2 CHN), 3.58 (sext, J=7.1 Hz, 1H, CH), 3.81 (s, 3H, CH$_3$), 4.01 (m, 2H, 2 CHN), 4.44 (s, 2H, NH$_2$), 6.24 (s, 1H, H$_{Ar}$), 7.67 (s, 1H, H$_{Ar}$).

IR (KBr, cm$^{-1}$): 3471.8, 3350.1, 3240.2, 2973.9, 2927.8, 2849.4, 1673.2, 1622.4, 1590.1, 1465.1, 1419.2, 1365.5, 1278.3, 1250.5, 1215.6, 1174.8.

Example 32

Tert-butyl 4-[3-(4-amino-5-fluoro-2-methoxyphenyl)-3-oxopropyl]piperidine-1-carboxylate Compound 32 is prepared according to the operating method of Example 30 described above, considering the following quantities:

Ethyl 3-(4-amino-5-fluoro-2-methoxyphenyl)-3-oxopropanoate: 185 mg (0.72 mmol)

Tert-butyl 4-(iodomethyl)piperidine-1-carboxylate: 283 mg (0.87 mmol)

K$_2$CO$_3$: 200 mg (1.45 mmol)

DMF: 5 ml

KOH: 187 mg (3.33 mmol)

EtOH: 10 ml

H$_2$O: 2 ml

The expected compound is obtained with a yield of 70% and is in the form of a white powder.

It has the following characteristics:

MP=171° C.

$C_{20}H_{29}FN_2O_4$

NMR $^1$H (CDCl$_3$): 1.11 (m, 2H, 2 CH), 1.43 (m, 1H, CH), 1.45 (s, 9H, 3 CH$_3$), 1.59 (m, 2H, CH$_2$), 1.67 (m, 2H, 2 CH), 2.67 (m, 2H, 2 CH), 2.92 (m, 2H, CH$_2$), 3.84 (s, 3H, CH$_3$), 4.08 (m, 2H, 2 CHN), 4.15 (s, 2H, NH$_2$), 6.27 (d, J$_{H-F}$=7.1 Hz, 1H, H$_{Ar}$), 7.94 (s, J$_{H-F}$=11.9 Hz, 1H, H$_{Ar}$).

IR (KBr, cm$^{-1}$): 3438.0, 3350.6, 3229.9, 2974.2, 2927.4, 2853.0, 1675.1, 1628.6, 1604.4, 1467.6, 1428.0, 1365.6, 1311.5, 1249.4, 1168.8.

Example 33

Tert-butyl 4-[3-(4-amino-5-bromo-2-methoxyphenyl)-3-oxopropyl]piperidine-1-carboxylate Compound 33 is prepared according to the operating method of Example 30 described above, considering the following quantities:

Ethyl 3-(4-amino-5-bromo-2-methoxyphenyl)-3-oxopropanoate: 250 mg (0.79 mmol)

tert-butyl 4-(iodomethyl)piperidine-1-carboxylate: 309 mg (0.95 mmol)

K$_2$CO$_3$: 218 mg (158 mmol)

DMF: 5 ml

KOH: 204 mg (3.63 mmol)

EtOH: 8 ml

H$_2$O: 2 ml

The expected compound is obtained with a yield of 68% and is in the form of a white powder.

It has the following characteristics:

MP=146-148° C.

$C_{20}H_{29}BrN_2O_4$

NMR $^1$H (CDCl$_3$): 1.07 (m, 2H, 2 CH), 1.43 (m, 10H, 3 CH$_3$, CH), 1.57 (m, 2H, CH$_2$), 1.64 (m, 2H, 2 CH), 2.64 (m, 2H, 2 CH), 2.88 (m, 2H, CH$_2$), 3.81 (s, 3H, CH$_3$), 4.06 (m, 2H, 2 CHN), 4.61 (s, 2H, NH$_2$), 6.25 (s, 1H, H$_{Ar}$), 7.91 (s, 1H, H$_{Ar}$).

IR (KBr, cm$^{-1}$): 3469.7, 3353.1, 3225.2, 2977.5, 2928.4, 2853.7, 1688.8, 1672.5, 1621.6, 1584.9, 1419.6, 1365.8, 1311.6, 1250.4, 1218.0, 1172.8.

Example 34

Tert-butyl 4-[3-(4-amino-5-iodo-2-methoxyphenyl)-3-oxopropyl]piperidine-1-carboxylate Compound 33 is prepared according to the operating method of Example 30 described above, considering the following quantities:

Ethyl 3-(4-amino-5-iodo-2-methoxyphenyl)-3-oxopropanoate: 172 mg (0.47 mmol)

Tert-butyl 4-(iodomethyl)piperidine-1-carboxylate: 169 mg (0.52 mmol)
$K_2CO_3$: 131 mg (0.95 mmol)
DMF: 5 ml
KOH: 122 mg (2.18 mmol)
EtOH: 8 ml
$H_2O$: 2 ml The expected compound is obtained with a yield of 65% and is in the form of a white powder.
It has the following characteristics:
MP=152° C.
$C_{20}H_{29}IN_2O_4$
NMR $^1H$ (CDCl$_3$): 1.10 (m, 2H, 2 CH), 1.45 (m, 10H, 3 CH$_3$, CH), 1.59 (m, 2H, CH$_2$), 1.67 (m, 2H, 2 CH), 2.67 (m, 2H, 2 CHN), 2.90 (m, 2H, CH$_2$), 3.85 (s, 3H, CH$_3$), 4.08 (m, 2H, 2 CHN), 4.51 (s, 2H, NH$_2$), 6.25 (s, 1H, H$_{Ar}$), 8.13 (s, 1H, H$_{Ar}$).
IR (KBr, cm$^{-1}$): 3459.4, 3341.2, 3219.9, 2972.8, 2928.5, 2850.1, 1672.7, 1621.3, 1578.9, 1451.4, 1415.0, 1365.2, 1265.5, 1217.3, 1164.6.

Example 35

Tert-butyl 4-[[(4-amino-5-bromo-2-methoxybenzoyl)amino]methyl]piperidine-1-carboxy-late 269 ml of Et$_3$N (1.93 mmol) and 414 mg of tert-butyl 4-(aminomethyl)piperidine-1-carboxylate (1.93 mmol) are added to a solution of 474 mg of 4-amino-5-bromo-2-methoxybenzoic acid (1.93 mmol) in 4 ml of DMF$^9$. The solution is held at −5° C. then 261 mg de HOBT (1.93 mmol) and 371 mg of EDCI.HCl (1.93 mmol) are added. The reaction medium is then stirred overnight at AT. The solution is diluted with water then extracted 3 times with AcOEt. The organic phases are combined then washed 4 times with water. The organic phase is dried over MgSO$_4$, filtered then concentrated. The reaction crude is then purified over silica gel (elution gradient: DCM to DCM/AcOEt 7/3) to obtain 630 mg of expected product (yield=74%).
MP=125° C.
$C_{19}H_{28}BrN_3O_4$RMN $^1H$ (CDCl$_3$): 1.17 (m, 2H, 2 CH), 1.45 (m, 9H, 3 CH$_3$), 1.75 (m, 3H, 3 CH), 2.69 (m, 2H, 2 CHN), 3.32 (m, 2H, CH$_2$N), 3.89 (s, 3H, CH$_3$), 4.10 (m, 2H, 2 CHN), 4.53 (s, 2H, NH$_2$), 6.32 (s, 1H, H$_{Ar}$), 7.76 (t, J=5.6 Hz, 1H, NH), 8.24 (s, 1H, H$_{Ar}$).
IR (KBr, cm$^{-1}$): 3448.2, 3337.2, 3206.8, 2970.9, 2927.7, 2854.9, 1689.0, 1631.6, 1593.5, 1559.2, 1491.2, 1465.4, 1430.2, 1364.5, 1247.0, 1179.2, 1147.3.

Example 36

Tert-butyl 4-[[(4-amino-5-iodo-2-methoxybenzoyl)amino]methyl]piperidine-1-carboxylate Compound 35 is prepared according to the operating method of Example 34 described above, considering the following quantities:
4-amino-5-iodo-2-methoxybenzoic acid: 342 mg (1.16 mmol)
Tert-butyl 4-(aminomethyl)piperidine-1-carboxylate: 214 mg (1.16 mmol)
Et$_3$N: 162 µl (1.16 mmol)
EDCI.HCl: 223 mg (1.16 mmol)
HOBT: 157 mg (1.16 mmol)
DMF: 5 ml
The expected compound is obtained with a yield of 80% and is in the form of a pale yellow powder.
It has the following characteristics:
MP=135° C.
$C_{19}H_{28}IN_3O_4$
NMR $^1H$ (CDCl$_3$): 1.18 (m, 2H, 2 CH), 1.45 (m, 9H, 3 CH$_3$), 1.73 (m, 3H, 3 CH), 2.69 (m, 2H, 2 CHN), 3.32 (m, 2H, CH$_2$N), 3.90 (s, 3H, CH$_3$), 4.12 (m, 2H, 2 CHN), 4.42 (s, 2H, NH$_2$), 6.28 (s, 1H, H$_{Ar}$), 7.72 (t, 1=5.8 Hz, 1H, NH), 8.45 (s, 1H, H$_{Ar}$).
IR (KBr, cm$^{-1}$): 3408.0, 3333.5, 3209.0, 2973.8, 2927.4, 2850.1, 1679.3, 1627.9, 1586.5, 1536.2, 1491.2, 1465.4, 1425.6, 1365.3, 1251.7, 1212.4, 1171.3, 1142.5.

The biological properties of the above-mentioned compounds according to the invention have been tested in order to determine:
their affinity as regards the 5-HT4 receptor
the power of their agonist effect as regards the 5-HT4 receptor
their inhibitory effect of acetylcholinesterase (Ellman test)
their interaction with the peripheral site of acetylcholinesterase (propidium displacement test)
their capacity to increase in vivo in the rodent the extinction time of the memory trace in an object recognition test modelling the episodic memory (nature of the object) of the rodent (object recognition test).

A) Affinity as Regards 5-HT4 Receptors

Equipment and Methods

Sampling Striatal Tissue and Membrane Preparation

All of the procedures described in this chapter are the result of the work of Grossman et al. (1993). In brief, the animals (Male Guinea pigs: 300-350 g, IFFA CREDO, France) are euthanized by decapitation then the brain is quickly removed at +4° C. The striatal regions are carefully dissected then reassembled. The striata assembly is placed in 10 volumes of 50 mM HEPES buffer, pH 7.4, at +4° C. After homogenisation at +4° C. (Ultra-Turrax, maximum speed, 15 sec) and ultracentrifugation (23 000 g, 60 min, +4° C.), the cell pellet is re-suspended in 50 mM, pH 7.4 buffer at +4° C. so as to obtain a tissue concentration in the order of 15 mg·ml$^{-1}$ (protein assay by the Lowry et al. method, 1951, using bovine serum albumin as a standard).

Competition Studies of the Products to be Studied in Competition Against [$^3$H]-GR113808

Prior to these competition studies, a series of saturation curves were performed in order to check whether the pharmacological parameters Kd, Bmax and the Hill Coefficient of [$^3$H]-GR113808, obtained in our experimental conditions, are consistent with those published in the literature. For that purpose, 7.5 µg/µL membrane preparation samples are incubated in duplicate (50 mM HEPES buffer, pH 7.4, +37° C.) at +37° C. for 30 minutes, in the presence of 7 increasing concentrations (0.05-1.5 nM, 200 µl of final volume) of [3H]-GR113808 (Grossman et al., 1993). Using a Brandel Cell Harvester, the binding of the radioligand with the proteins is interrupted by rapid filtration of the incubation medium through a filter strip (WHATMAN GF/B FP-100) pre-incubated in polyethylenimine (PEI 0.5% in water); filtration is followed by 3 rinses with 4 ml of 50 mM HEPES buffer, pH 7.4, at +4° C. The non-specific binding of [$^3$H]-GR113808 is quantified in the presence of 30 µM of serotonin, specific binding thus being estimated as the difference: (binding in the absence of serotonin)−(binding in the presence of serotonin).

The competition studies are carried out with 0.1 nM of [$^3$H]-GR113808 in the presence of 10$^{-6}$ or 10$^{-8}$ M, or n concentrations for the Kis, of ligand to be studied, prucalopride being used as the reference 5-HT4 agonist. After incubation, the filtration and rinsing procedures were identical to those described above.

Results

By way of example, the affinities of several compounds according to the invention as regards 5-HT4 receptors are listed in Table 4.

TABLE 4

Affinity of several compounds according to the invention as regards 5-HT4 receptors, prucalopride being taken as a reference (Ki in nM).

| Compound | Ki in nM |
|---|---|
| 1 | 88.6 |
| 2 | 8.9 |
| 3 | 44.7 |
| 4 | 125.0 |
| 5 | 3.8 |
| 6 | 14.8 |
| 7 | 8.8 |
| 8 | 3.0 |
| 9 | 7.1 |
| 10 | 125.0 |
| 11 | 8.0 |
| 12 | 3.9 |
| 13 | 2.5 |
| 14 | 17.0 |
| 15 | 18.1 |
| 16 | 8.2 |
| 17 | 2.3 |
| 18 | 5.4 |
| 19 | 13.9 |
| 20 | 0.9 |
| 21 | 125.0 |
| 22 | 12.5 |
| 23 | 2.5 |
| 24 | 13.1 |
| prucalopride | 44.1 |

B) Agonist Nature as Regards the 5-HT4 Receptor

Equipment and Methods

The agonist nature as regards the 5-HT4 receptor of several compounds according to the invention is determined by the measurement of the accumulation of intracellular cyclic AMP. For this, transfected stable cells are cultivated until confluence with a serum-free medium 4 h before the start of the experiment. The cells are then pre-incubated for 15 minutes in a serum-free medium supplemented with 5 mM of theophylline, 10 µM of pargyline and 1 µM of GR127935 compound in CHO cells to block the endogenous activity of the 5-HT1B receptors. Serotonin is then added for 15 more minutes. The reaction is stopped by aspiration of the medium and the addition of 500 µL of ice-cold ethanol. After 30 min of incubation, the ethanolic fraction is collected and evaporated under vacuum. The pellet is then reconstituted and the cyclic AMP is quantified by radioimmunoassay (cyclic AMP competitive radioimmunoassay, Immunotech, Marseille, France). The Student Tests are performed using QuickTest software. The results are expressed as a percentage of agonist effect in relation to serotonin. Prucalopride, a full 5-HT4 receptor agonist, is used as a reference.

Results

By way of example, the powers of agonist effect of several compounds according to the invention as regards 5-HT4 receptors are shown in Table 5.

TABLE 5

Power of the agonistic effect of several compounds according to the invention as regards 5-HT4 receptors (%).

| Compound | Agonistic effect % |
|---|---|
| 5 | 16% |
| 8 | 12% |
| 9 | 22% |
| 12 | 21% |
| prucalopride | 100% |

C) Ellman Test

Equipment and Methods

Acetylcholinesterase extracted from human erythrocytes (buffered aqueous solution, ≥500 units/mg, Sigma Aldrich) is diluted in a 20 mM HEPES buffer pH8, 0.1% Triton X-100, to obtain a standard solution with 2.5 units of enzyme activity/ml. 100 µL of a 0.3 mM 5,5-dithiobis(2-nitrobenzoic acid) (DTNB) solution in a pH 7.4 phosphate buffer are introduced into a 96-well plate, followed by 50 µL of compound to be tested in solution in DMSO and 50 µL of enzyme solution. After 5 min of preincubation, the reaction is initiated by injecting 50 µL of 10 mM acetylthiocholine iodide solution. Hydrolysis of the acetylthiocholine is followed by the formation of the anion 5-thio-2-nitrobenzoate, produced by the reaction of the DTNB with the thiocholine released by the enzymatic hydrolysis of the acetylthiocholine, by means of a microplate reader (TECAN Infinite M200, Lyon, France) at a wavelength of 412 nm per minute for 10 minutes. Donepezil is used as a reference product.

For compounds showing a significant inhibition of acetylcholinesterase (≥50%) after 4 min of reaction, the values of $IC_{50}$ are measured graphically at six points on the inhibition curve by Origin software.

Results

By way of example, the inhibitory activities of human acetylcholinesterase of several compounds according to the invention as regards 5-HT4 receptors are show in Table 6.

TABLE 6

Inhibition of human acetylcholinesterase of several compounds according to the invention, Donepezil being used as a reference ($IC_{50}$ in nM).

| Compound | $IC_{50}$ in nM |
|---|---|
| 1 | 748 |
| 2 | 445 |
| 3 | 658 |
| 4 | 26 |
| 5 | 24 |
| 6 | 937 |
| 7 | 577 |
| 8 | 69 |
| 9 | 63 |
| 10 | 201 |
| 11 | 321 |
| 12 | 57 |
| 13 | 118 |
| 14 | 99 |
| 15 | 304 |
| 16 | 222 |
| 17 | 3730 |
| 18 | 8700 |
| 19 | 5090 |
| 20 | 2720 |
| 21 | 411 |
| 22 | 395 |
| 23 | 625 |
| 24 | 320 |
| Donepezil | 11 |

D) Propidium Displacement Test
Equipment and Methods

When propidium diiodide binds to the peripheral site of AChE, it produces an increase in fluorescence which can be used as proof of its binding to the enzyme. Fluorescence measurements are made in 200 µL of solution in 96-well plates using a Tecan Infinite M2000 microplate reader. Five units of eeAChE are incubated for 15 min at 25° C. in a 1 mM Tris-HCl, pH 8.0, buffer with 150 µL of $10^{-5}$M solution of compounds to be tested or Donepezil as a reference. 50 µL of micromolar solution of propidium diiodide are added before measuring fluorescence. The excitation wavelength is measured at 535 nm, and the emission wavelength at 595 nm. Each test is repeated at least three times.

Results

By way of example, the propidium diiodide displacement values of the peripheral site of eeAChE of several compounds according to the invention are shown in Table 7.

TABLE 7

Propidium diiodide displacement from the peripheral site of eeAChE of several compounds according to the invention (%)

| Compound | % Propidium Displacement |
|---|---|
| 5 | 22% |
| 8 | 20% |
| 9 | 22% |
| 12 | 20% |
| 14 | 20% |
| 16 | 21% |
| 23 | 22% |
| Donepezil | 23% |

E) Object Recognition Test
Equipment and Methods
Animals

The tests are performed using male NMRI mice of around 3 months old at the time of the tests. These mice are kept in groups of 15 in standard polycarbonate cages (42×29×15 cm³), in an animal housing facility kept at a temperature of 22±2° C. and relative humidity of 55±10%. They have free access to food and water and are kept in a reverse cycle (light phase between 20.00 and 8.00) to enable experiments to be performed during their phase of activity.

Object Recognition Test

The object recognition test is based on the spontaneous preference of rodents for novelty, without bringing food deprivation or electric shock into play. This test allows a form of episodic memory in the rodent to be assessed in the sense that the ability of the animal to store information connected with a spatio-temporal context is assessed (Dere et al., 2007).

The device comprises a square PVC enclosure (33×33×20 cm, illuminated at 10 lux in the center) with black surfaces. The test is performed in 2 phases: one habituation phase, allowing the animals to become habituated to the test environment (enclosure, room, experimenter), the other a memory performance assessment phase. A camera is positioned above the device and connected to a video-tracking system (ViewPoint®). During the behavioral tests, the experimenter is not present in the experimentation room but remains in an adjacent room that houses the video-tracking system.

After a habituation phase (Day 1, individual exposure for 5 minutes to the open-field with no objects), the memory performance assessment phase begins on the 2nd day and is made up of 2 sessions, one the presentation session and the other the test session. Immediately before the presentation session, the mouse is habituated again with the equipment for one minute, then two identical objects, A1 and A2, are placed at about 5 cm from the walls of the enclosure. The mouse is placed with its back to the objects, facing the experimenter, and freely explores the device. The session is stopped when the mouse reaches a total exploration time of the two objects of 30 seconds. The exploration time of each object, A1 and A2 respectively, as well as the time required to achieve the exploration criterion are measured. After an intersession period of 24 hours, a test session is performed. Two objects are used: one familiar object A3 (a copy of A1 or A2 not previously presented) and one object B, different from object A, which will constitute the new object. The session is stopped by the experimenter when the mouse achieves a total exploration criterion of 30 seconds. The time required to achieve the exploration criterion as well as the exploration time of the new object are measured and the latter is compared to the chance level (15 s).

The objects used on the test day are a blue ceramic dolphin (4 cm in diameter and 10 cm high) and a transparent bottle filled with sand (3×4.5×9 cm), available in four copies, which are cleaned after each use (70% ethanol). These objects are glued to the floor of the open field with Patafix® so that the mice cannot move them. The combinations of objects (bottle/bottle and dolphin/dolphin) and the placing of a new object (left/right) are determined at random to avoid bias due to a possible preference for an object or place.

The results are expressed by the exploration percentage of each object during the test session. The data are analyzed by an analysis of variance (ANOVA) with repeated measurements, followed by a Student-Newman-Keuls (SNK) multiple comparison test.

Administration of the Compounds

Batches of 10 to 12 mice are formed into an experimental group. The compounds in solution in the physiological serum are administered intraperitoneally (volume of injection, 10 ml/kg of body weight), 30 minutes before the acquisition session. A control batch (physiological serum) is created.

Results (FIG. 1)

By way of example, Compound 9 results in an improvement in object recognition performance compared to the control batch with a maximum effect after the dose of 0.3 mg/kg

What is claimed is:
1. A compound of the general formula (I):

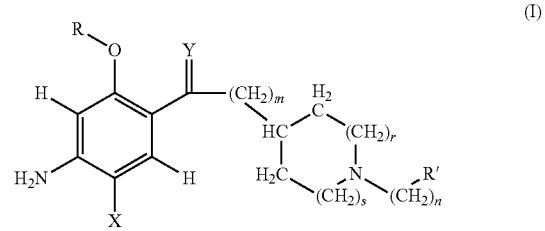

wherein:
X represents
  a hydrogen atom,
  a halogen atom (Hal), where (Hal) is fluorine, chlorine, bromine or iodine, or a straight- or branched-chain $C_pHal_{2p+1}$ polyhalogenoalkyl group, where p=1, 2, 3 or 4, (Hal) having the same meaning as indicated above;

Y represents
an oxygen atom,
a sulfur atom, or
an N—R" radical where R" represents a hydrogen atom, an —OH radical or a straight- or branched-chain $C_qH_{2q+1}$ alkyl radical, where q=1, 2, 3 or 4;

m has a value of 1, 2 or 3;
n has a value of 0, 1, 2 or 3;
r and s have values selected from r=s=0; r=s=1; r=s=2; r=0 and s=1; and r=0 and s=2;

R represents
a hydrogen atom,
a straight- C1-C5 alkyl group, a branched-chain C1-C5 alkyl group, a straight- C1-C5 fluoro-alkyl group, or branched-chain C1-C5 fluoro-alkyl group;

R' represents
a C3-C10 cycloalkyl or heterocyclic alkyl group, optional substituted by —R, where the heteroatom is oxygen, nitrogen, or sulfur; or
a C5-C13 bicyclicalkyl or heterobicyclic alkyl group, optionally substituted by —R, where the heteroatom is oxygen, nitrogen, or sulfur.

2. The compound of claim 1, wherein X in the formula (I) represents a halogen atom.

3. The compound of claim 1, Y in the formula (I) represents an oxygen atom.

4. The compound of claim 1, wherein all of the coefficients n, r and s in the formula (I) have the value 1.

5. The compound of claim 1, wherein R in the formula (I) represents H, $CH_3$, $CH_2CH_3$ or $CH_2$—$CH_2F$.

6. The compound of claim 1, wherein R' in the formula (I) represents a radical taken from the group formed by the radicals cyclopropyl, cyclobutyl, cyclopentyl, cyclohexyl, and 4-piperidine.

7. The compound of claim 2, wherein R is a methyl radical and R' is a $C_4$-$C_7$ cycloalkyl radical.

8. A pharmaceutical composition that comprises, as an active ingredient, at least one compound according to claim 1.

9. The pharmaceutical composition of claim 8, wherein the pharmaceutical composition contains a pharmaceutically acceptable excipient.

10. The pharmaceutical composition of claim 8, wherein the pharmaceutical composition further comprises a second active ingredient having an inhibitory action of acetylcholinesterase and chosen from the group consisting of:
   a) 1,2,3,4-Tetrahydroacridin-9-amine,
   b) (RS)-2-[(1-benzyl-4-piperidyl)methyl-5,6-dimethoxy-2,3-dihydroinden-1-one,
   c) (S)—N-ethyl-N-methyl-3-[(1-dimethylamino)ethyl]-phenyl carbamate, and
   d) 4aS,6R,8aS)-5,6,9,10,11,12-hexahydro-3-methoxy-11-methyl-4aH-[1]benzofuro [3a,3,2-ef][2]benzazepin-6-ol.

11. The pharmaceutical composition of claim 8, wherein the pharmaceutical composition further comprises at least one partial 5-HT4 receptor agonist chosen from the group consisting of:
   a) 1-(4-amino-5-chloro-2-methoxyphenyl)-2-[1-butyl-4-piperidyl]propan-1 one, and
   b) N-(2-(4-(3-(4-amino-5-chloro-3-methoxyphenyl)-3-oxypropyl)piperidin-1-yl)ethyl)methane sulfonamide,
the said agonist being in a molar ratio of between 10/90 and 90/10 in relation to the compound according to claim 1.

12. The pharmaceutical composition of claim 8, designed to be administered to mammals and having a promnesiant effect used for the treatment of neurological diseases with amnestic deficit.

13. The pharmaceutical composition of claim 8, that can be used for treatment of Alzheimer's disease in a human subject.

14. The pharmaceutical composition of claim 8 further comprising the compound according to claim 1 in a mixture with dispersion agents, softening agents, suspension agents, sweeteners or flavor enhancers.

\* \* \* \* \*